US012605086B2

(12) United States Patent
Walker et al.

(10) Patent No.: US 12,605,086 B2
(45) **Date of Patent: *Apr. 21, 2026**

(54) FLEXIBLE INSTRUMENT LOCALIZATION FROM BOTH REMOTE AND ELONGATION SENSORS

(71) Applicant: Auris Health, Inc., Redwood City, CA (US)

(72) Inventors: Sean Walker, Mountain View, CA (US); Dave Camarillo, Aptos, CA (US); Matt Roelle, Sunnyvale, CA (US); Christopher Sewell, Sunnyvale, CA (US); Aditya Koolwal, San Francisco, CA (US)

(73) Assignee: Auris Health, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/680,047

(22) Filed: May 31, 2024

(65) Prior Publication Data

US 2024/0315590 A1 Sep. 26, 2024

Related U.S. Application Data

(63) Continuation of application No. 17/881,759, filed on Aug. 5, 2022, now Pat. No. 12,016,669, which is a
(Continued)

(51) Int. Cl.
*A61B 6/12* (2006.01)
*A61B 5/00* (2006.01)
(Continued)

(52) U.S. Cl.
CPC ........... *A61B 5/061* (2013.01); *A61B 5/0071* (2013.01); *A61B 5/7225* (2013.01); *A61B 6/12* (2013.01);
(Continued)

(58) Field of Classification Search
CPC .. A61B 6/12; A61B 6/487; A61B 5/06; A61B 5/061–068; A61B 2034/2059; A61B 2034/2061; A61B 2034/2064
See application file for complete search history.

(56) References Cited

U.S. PATENT DOCUMENTS 4,745,908 A 5/1988 Wardle
5,273,025 A 12/1993 Sakiyam et al.
(Continued)

FOREIGN PATENT DOCUMENTS

CN 101147676 A 3/2008
CN 101222882 A 7/2008
(Continued)

OTHER PUBLICATIONS

Al-Ahmad, Amin, Jessica D. Grossman, and Paul J. Wang. "Early experience with a computerized robotically controlled catheter system." *Journal of Interventional Cardiac Electrophysiology* 12 (2005): 199-202.
(Continued)

*Primary Examiner* — Colin T. Sakamoto
(74) *Attorney, Agent, or Firm* — FBT Gibbons LLP

(57) ABSTRACT

A system and method of tracking a flexible elongate instrument within a patient is disclosed herein. The system is configured to obtain remote localization measurement data of the flexible elongate instrument and obtain elongation measurement data of the flexible elongate instrument. This data is combined and transformed to a coordinate reference frame to produce a localization of the flexible elongate instrument that is more accurate than the remote localization measurements or elongation measurement data alone. The combined localization is then provided to a localization consumer.

20 Claims, 8 Drawing Sheets

Related U.S. Application Data continuation of application No. 15/056,652, filed on Feb. 29, 2016, now Pat. No. 11,426,095, which is a continuation of application No. 13/833,733, filed on Mar. 15, 2013, now Pat. No. 9,271,663.

(51) Int. Cl.

| | |
|---|---|
| *A61B 5/06* | (2006.01) |
| *A61B 6/00* | (2006.01) |
| *A61B 34/20* | (2016.01) |

(52) U.S. Cl.

CPC .............. *A61B 6/487* (2013.01); *A61B 34/20* (2016.02); *A61B 5/062* (2013.01); *A61B 2034/2051* (2016.02); *A61B 2034/2061* (2016.02); *A61B 2034/2065* (2016.02)

(56) References Cited

U.S. PATENT DOCUMENTS

| | | | |
|---|---|---|---|
| 5,398,691 | A | 3/1995 | Martin et al. |
| 5,408,409 | A | 4/1995 | Glassman et al. |
| 5,524,180 | A | 6/1996 | Wang et al. |
| 5,526,812 | A | 6/1996 | Dumoulin et al. |
| 5,550,953 | A | 8/1996 | Seraji |
| 5,553,611 | A | 9/1996 | Budd et al. |
| 5,558,091 | A | 9/1996 | Acker et al. |
| 5,631,973 | A | 5/1997 | Green |
| 5,636,255 | A | 6/1997 | Ellis |
| 5,713,946 | A | 2/1998 | Ben-Haim |
| 5,729,129 | A | 3/1998 | Acker |
| 5,749,362 | A | 5/1998 | Funda et al. |
| 5,831,614 | A | 11/1998 | Tognazzini et al. |
| 5,859,934 | A | 1/1999 | Green |
| 5,873,822 | A | 2/1999 | Ferre et al. |
| 5,876,325 | A | 3/1999 | Mizuno et al. |
| 5,902,239 | A | 5/1999 | Buurman |
| 5,920,319 | A | 7/1999 | Vining et al. |
| 5,935,075 | A | 8/1999 | Casscells |
| 5,951,475 | A | 9/1999 | Gueziec et al. |
| 6,016,439 | A | 1/2000 | Acker |
| 6,019,724 | A | 2/2000 | Gronningsaeter et al. |
| 6,038,467 | A | 3/2000 | De Bliek et al. |
| 6,047,080 | A | 4/2000 | Chen |
| 6,059,718 | A | 5/2000 | Taniguchi et al. |
| 6,063,095 | A | 5/2000 | Wang et al. |
| 6,167,292 | A | 12/2000 | Badano |
| 6,203,493 | B1 | 3/2001 | Ben-Haim |
| 6,226,543 | B1 | 5/2001 | Gilboa et al. |
| 6,233,476 | B1 | 5/2001 | Strommer et al. |
| 6,246,784 | B1 | 6/2001 | Summers |
| 6,246,898 | B1 | 6/2001 | Vesely |
| 6,253,770 | B1 | 7/2001 | Acker et al. |
| 6,259,806 | B1 | 7/2001 | Green |
| 6,272,371 | B1 | 8/2001 | Shlomo |
| 6,332,089 | B1 | 12/2001 | Acker |
| 6,424,885 | B1 | 7/2002 | Niemeyer et al. |
| 6,425,865 | B1 | 7/2002 | Salcudean et al. |
| 6,466,198 | B1 | 10/2002 | Feinstein |
| 6,490,467 | B1 | 12/2002 | Bucholz |
| 6,553,251 | B1 | 4/2003 | Lähdesmäki |
| 6,592,520 | B1 | 7/2003 | Peszynski |
| 6,593,884 | B1 | 7/2003 | Gilboa et al. |
| 6,665,554 | B1 | 12/2003 | Charles |
| 6,690,963 | B2 | 2/2004 | Ben-Haim |
| 6,690,964 | B2 | 2/2004 | Beiger et al. |
| 6,711,429 | B1 | 3/2004 | Gilboa et al. |
| 6,726,675 | B1 | 4/2004 | Beyar |
| 6,782,287 | B2 | 8/2004 | Grzeszczuk et al. |
| 6,812,842 | B2 | 11/2004 | Dimmer |
| 6,892,090 | B2 | 5/2005 | Verard et al. |
| 6,899,672 | B2 | 5/2005 | Chin |
| 6,926,709 | B2 | 8/2005 | Beiger et al. |
| 6,994,094 | B2 | 2/2006 | Schwartz |
| 6,996,430 | B1 | 2/2006 | Gilboa et al. |
| 7,155,315 | B2 | 12/2006 | Niemeyer et al. |
| 7,180,976 | B2 | 2/2007 | Wink |
| 7,206,627 | B2 | 4/2007 | Abovitz |
| 7,233,820 | B2 | 6/2007 | Gilboa |
| 7,386,339 | B2 | 6/2008 | Strommer et al. |
| 7,756,563 | B2 | 7/2010 | Higgins |
| 7,850,642 | B2 | 12/2010 | Moll et al. |
| 7,901,348 | B2 | 3/2011 | Soper |
| 8,052,621 | B2 | 11/2011 | Wallace et al. |
| 8,092,397 | B2 | 1/2012 | Wallace et al. |
| 8,155,403 | B2 | 4/2012 | Tschirren et al. |
| 8,190,238 | B2 | 5/2012 | Moll et al. |
| 8,298,135 | B2 | 10/2012 | Ito et al. |
| 8,317,746 | B2 | 11/2012 | Sewell et al. |
| 8,388,556 | B2 | 3/2013 | Wallace et al. |
| 8,394,054 | B2 | 3/2013 | Wallace et al. |
| 8,460,236 | B2 | 6/2013 | Roelle et al. |
| 8,657,781 | B2 | 2/2014 | Sewell et al. |
| 8,672,837 | B2 | 3/2014 | Roelle et al. |
| 8,821,376 | B2 | 9/2014 | Tolkowsky |
| 8,858,424 | B2 | 10/2014 | Hasegawa |
| 8,929,631 | B2 | 1/2015 | Pfister et al. |
| 9,014,851 | B2 | 4/2015 | Wong et al. |
| 9,039,685 | B2 | 5/2015 | Larkin et al. |
| 9,057,600 | B2 | 6/2015 | Walker et al. |
| 9,125,639 | B2 | 9/2015 | Mathis |
| 9,138,129 | B2 | 9/2015 | Diolaiti |
| 9,173,713 | B2 | 11/2015 | Hart et al. |
| 9,183,354 | B2 | 11/2015 | Baker et al. |
| 9,186,046 | B2 | 11/2015 | Ramamurthy et al. |
| 9,271,663 | B2 | 3/2016 | Walker et al. |
| 9,272,416 | B2 | 3/2016 | Hourtash et al. |
| 9,283,046 | B2 | 3/2016 | Walker et al. |
| 9,289,578 | B2 | 3/2016 | Walker et al. |
| 9,459,087 | B2 | 10/2016 | Dunbar |
| 9,498,291 | B2 | 11/2016 | Balaji et al. |
| 9,498,601 | B2 | 11/2016 | Tanner et al. |
| 9,504,604 | B2 | 11/2016 | Alvarez |
| 9,532,840 | B2 | 1/2017 | Wong et al. |
| 9,561,083 | B2 | 2/2017 | Yu et al. |
| 9,566,414 | B2 | 2/2017 | Wong et al. |
| 9,603,668 | B2 | 3/2017 | Weingarten et al. |
| 9,622,827 | B2 | 4/2017 | Yu |
| 9,629,595 | B2 | 4/2017 | Walker et al. |
| 9,629,682 | B2 | 4/2017 | Wallace et al. |
| 9,636,184 | B2 | 5/2017 | Lee et al. |
| 9,710,921 | B2 | 7/2017 | Wong et al. |
| 9,713,509 | B2 | 7/2017 | Schuh et al. |
| 9,717,563 | B2 | 8/2017 | Tognaccini et al. |
| 9,726,476 | B2 | 8/2017 | Ramamurthy et al. |
| 9,727,963 | B2 | 8/2017 | Mintz et al. |
| 9,737,371 | B2 | 8/2017 | Roma et al. |
| 9,737,373 | B2 | 8/2017 | Schuh |
| 9,744,335 | B2 | 8/2017 | Jiang |
| 9,763,741 | B2 | 9/2017 | Alvarez et al. |
| 9,788,910 | B2 | 10/2017 | Schuh |
| 9,827,061 | B2 | 11/2017 | Balaji et al. |
| 9,844,353 | B2 | 12/2017 | Walker et al. |
| 9,844,412 | B2 | 12/2017 | Bogusky et al. |
| 9,867,635 | B2 | 1/2018 | Alvarez et al. |
| 9,918,681 | B2 | 3/2018 | Wallace et al. |
| 9,931,025 | B1 | 4/2018 | Graetzel et al. |
| 9,949,749 | B2 | 4/2018 | Noonan et al. |
| 9,955,986 | B2 | 5/2018 | Shah |
| 9,962,228 | B2 | 5/2018 | Schuh et al. |
| 9,980,785 | B2 | 5/2018 | Schuh |
| 9,993,313 | B2 | 6/2018 | Schuh et al. |
| 10,016,900 | B1 | 7/2018 | Meyer et al. |
| 10,022,192 | B1 | 7/2018 | Ummalaneni |
| 10,123,755 | B2 | 11/2018 | Walker et al. |
| 10,130,427 | B2 | 11/2018 | Tanner et al. |
| 10,136,950 | B2 | 11/2018 | Schoenefeld |
| 10,145,747 | B1 | 12/2018 | Lin et al. |
| 10,159,532 | B1 | 12/2018 | Ummalaneni et al. |
| 10,278,778 | B2 | 5/2019 | State |
| 10,299,870 | B2 | 5/2019 | Connolly et al. |
| 10,482,599 | B2 | 11/2019 | Mintz et al. |
| 10,517,692 | B2 | 12/2019 | Eyre et al. |
| 10,524,866 | B2 | 1/2020 | Srinivasan |

(56)                    References Cited

U.S. PATENT DOCUMENTS

| | | | |
|---|---|---|---|
| 10,639,114 B2 | 5/2020 | Schuh |
| 10,667,875 B2 | 6/2020 | DeFonzo |
| 10,743,751 B2 | 8/2020 | Landey et al. |
| 10,751,140 B2 | 8/2020 | Wallace et al. |
| 10,765,303 B2 | 9/2020 | Graetzel et al. |
| 10,765,487 B2 | 9/2020 | Ho |
| 11,426,095 B2 | 8/2022 | Walker et al. |
| 2001/0021843 A1 | 9/2001 | Bosselmann et al. |
| 2001/0039421 A1 | 11/2001 | Heilbrun |
| 2002/0065455 A1 | 5/2002 | Ben-Haim et al. |
| 2002/0077533 A1 | 6/2002 | Bieger et al. |
| 2002/0120188 A1 | 8/2002 | Brock et al. |
| 2003/0105603 A1 | 6/2003 | Hardesty |
| 2003/0125622 A1 | 7/2003 | Schweikard et al. |
| 2003/0135204 A1 | 7/2003 | Lee et al. |
| 2003/0181809 A1 | 9/2003 | Hall et al. |
| 2003/0195664 A1 | 10/2003 | Nowlin et al. |
| 2004/0047044 A1 | 3/2004 | Dalton |
| 2004/0072066 A1 | 4/2004 | Cho et al. |
| 2004/0186349 A1 | 9/2004 | Ewers |
| 2004/0249267 A1 | 12/2004 | Gilboa |
| 2004/0263535 A1 | 12/2004 | Birkenbach et al. |
| 2005/0004516 A1 | 1/2005 | Vanney |
| 2005/0027397 A1 | 2/2005 | Niemeyer |
| 2005/0033149 A1 | 2/2005 | Strommer et al. |
| 2005/0060006 A1 | 3/2005 | Pflueger |
| 2005/0085714 A1 | 4/2005 | Foley et al. |
| 2005/0107679 A1 | 5/2005 | Geiger |
| 2005/0143649 A1 | 6/2005 | Minai et al. |
| 2005/0143655 A1 | 6/2005 | Satoh |
| 2005/0171508 A1 | 8/2005 | Gilboa |
| 2005/0182295 A1 | 8/2005 | Soper et al. |
| 2005/0193451 A1 | 9/2005 | Quistgaard et al. |
| 2005/0256398 A1 | 11/2005 | Hastings |
| 2005/0272975 A1 | 12/2005 | McWeeney et al. |
| 2006/0004286 A1 | 1/2006 | Chang |
| 2006/0015096 A1 | 1/2006 | Hauck et al. |
| 2006/0025668 A1 | 2/2006 | Peterson |
| 2006/0025676 A1 | 2/2006 | Viswanathan et al. |
| 2006/0058643 A1 | 3/2006 | Florent |
| 2006/0076023 A1 | 4/2006 | Rapacki et al. |
| 2006/0084860 A1 | 4/2006 | Geiger |
| 2006/0095066 A1 | 5/2006 | Chang et al. |
| 2006/0098851 A1 | 5/2006 | Shoham et al. |
| 2006/0149134 A1 | 7/2006 | Soper et al. |
| 2006/0173290 A1 | 8/2006 | Lavallee et al. |
| 2006/0184016 A1 | 8/2006 | Glossop |
| 2006/0209019 A1 | 9/2006 | Hu |
| 2006/0241465 A1 | 10/2006 | Huennekens et al. |
| 2006/0258935 A1 | 11/2006 | Pile-Spellman et al. |
| 2006/0258938 A1 | 11/2006 | Hoffman et al. |
| 2007/0015997 A1 | 1/2007 | Higgins et al. |
| 2007/0032826 A1 | 2/2007 | Schwartz |
| 2007/0055128 A1 | 3/2007 | Glossop |
| 2007/0055144 A1 | 3/2007 | Neustadter |
| 2007/0073136 A1 | 3/2007 | Metzger |
| 2007/0083193 A1 | 4/2007 | Werneth et al. |
| 2007/0123748 A1 | 5/2007 | Meglan |
| 2007/0135886 A1 | 6/2007 | Maschke |
| 2007/0156019 A1 | 7/2007 | Larkin et al. |
| 2007/0167743 A1 | 7/2007 | Honda |
| 2007/0167801 A1 | 7/2007 | Webler et al. |
| 2007/0208252 A1 | 9/2007 | Makower |
| 2007/0225559 A1 | 9/2007 | Clerc et al. |
| 2007/0249901 A1 | 10/2007 | Ohline et al. |
| 2007/0253599 A1 | 11/2007 | White et al. |
| 2007/0269001 A1 | 11/2007 | Maschke |
| 2007/0276180 A1 | 11/2007 | Greenburg et al. |
| 2007/0287992 A1 | 12/2007 | Diolaiti et al. |
| 2007/0293721 A1 | 12/2007 | Gilboa |
| 2007/0299353 A1 | 12/2007 | Harley et al. |
| 2008/0071140 A1 | 3/2008 | Gattani |
| 2008/0079421 A1 | 4/2008 | Jensen |
| 2008/0103389 A1 | 5/2008 | Begelman et al. |
| 2008/0118118 A1 | 5/2008 | Berger |
| 2008/0118135 A1 | 5/2008 | Averbach |
| 2008/0123921 A1 | 5/2008 | Gielen et al. |
| 2008/0147089 A1 | 6/2008 | Loh |
| 2008/0161681 A1 | 7/2008 | Hauck |
| 2008/0183064 A1 | 7/2008 | Chandonnet et al. |
| 2008/0183068 A1 | 7/2008 | Carls et al. |
| 2008/0183073 A1 | 7/2008 | Higgins et al. |
| 2008/0183188 A1 | 7/2008 | Carts et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0243142 A1 | 10/2008 | Gildenberg |
| 2008/0262297 A1 | 10/2008 | Gilboa |
| 2008/0275349 A1 | 11/2008 | Halperin |
| 2008/0287963 A1 | 11/2008 | Rogers et al. |
| 2008/0306490 A1 | 12/2008 | Lakin et al. |
| 2008/0312501 A1 | 12/2008 | Hasegawa et al. |
| 2009/0030307 A1 | 1/2009 | Govari |
| 2009/0054729 A1 | 2/2009 | Mori |
| 2009/0076476 A1 | 3/2009 | Barbagli et al. |
| 2009/0149867 A1 | 6/2009 | Glozman |
| 2009/0227861 A1 | 9/2009 | Ganatra |
| 2009/0248036 A1 | 10/2009 | Hoffman et al. |
| 2009/0259230 A1 | 10/2009 | Khadem |
| 2009/0262109 A1 | 10/2009 | Markowitz et al. |
| 2009/0292166 A1 | 11/2009 | Ito |
| 2009/0295797 A1 | 12/2009 | Sakaguchi |
| 2010/0008555 A1 | 1/2010 | Trumer et al. |
| 2010/0039506 A1 | 2/2010 | Sarvestani et al. |
| 2010/0041949 A1 | 2/2010 | Tolkowsky |
| 2010/0054536 A1 | 3/2010 | Huang |
| 2010/0121139 A1 | 5/2010 | Yang et al. |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0225209 A1 | 9/2010 | Goldberg |
| 2010/0240989 A1 | 9/2010 | Stoianovici |
| 2010/0290530 A1 | 11/2010 | Huang et al. |
| 2010/0292565 A1 | 11/2010 | Meyer |
| 2010/0298641 A1 | 11/2010 | Tanaka |
| 2010/0328455 A1 | 12/2010 | Nam et al. |
| 2011/0054303 A1 | 3/2011 | Barrick |
| 2011/0092808 A1 | 4/2011 | Shachar |
| 2011/0113852 A1 | 5/2011 | Prisco |
| 2011/0184238 A1 | 7/2011 | Higgins |
| 2011/0234780 A1 | 9/2011 | Ito |
| 2011/0238082 A1 | 9/2011 | Wenderow |
| 2011/0245665 A1 | 10/2011 | Nentwick |
| 2011/0248987 A1 | 10/2011 | Mitchell |
| 2011/0249016 A1 | 10/2011 | Zhang |
| 2011/0276179 A1 | 11/2011 | Banks et al. |
| 2011/0295247 A1 | 12/2011 | Schlesinger et al. |
| 2011/0295267 A1 | 12/2011 | Tanner et al. |
| 2011/0295268 A1 | 12/2011 | Roelle et al. |
| 2011/0319815 A1 | 12/2011 | Roelle et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0062714 A1 | 3/2012 | Liu |
| 2012/0065481 A1 | 3/2012 | Hunter |
| 2012/0069167 A1 | 3/2012 | Liu et al. |
| 2012/0071782 A1 | 3/2012 | Patil et al. |
| 2012/0082351 A1 | 4/2012 | Higgins |
| 2012/0116253 A1 | 5/2012 | Wallace et al. |
| 2012/0120305 A1 | 5/2012 | Takahashi |
| 2012/0165656 A1 | 6/2012 | Montag |
| 2012/0191079 A1 | 7/2012 | Moll et al. |
| 2012/0209069 A1 | 8/2012 | Popovic |
| 2012/0215094 A1 | 8/2012 | Rahimian et al. |
| 2012/0219185 A1 | 8/2012 | Hu |
| 2012/0289777 A1 | 11/2012 | Chopra |
| 2012/0289783 A1 | 11/2012 | Duindam et al. |
| 2012/0302869 A1 | 11/2012 | Koyrakh et al. |
| 2013/0060146 A1 | 3/2013 | Yang et al. |
| 2013/0072787 A1 | 3/2013 | Wallace et al. |
| 2013/0096377 A1 | 4/2013 | Duindam et al. |
| 2013/0144116 A1 | 6/2013 | Cooper et al. |
| 2013/0165945 A9 | 6/2013 | Roelle |

(56) References Cited

U.S. PATENT DOCUMENTS

| 2013/0204124 A1 | 8/2013 | Duindam |
| 2013/0225942 A1 | 8/2013 | Holsing |
| 2013/0243153 A1 | 9/2013 | Sra |
| 2013/0246334 A1 | 9/2013 | Ahuja |
| 2013/0259315 A1 | 10/2013 | Angot et al. |
| 2013/0303892 A1 | 11/2013 | Zhao |
| 2013/0345718 A1 | 12/2013 | Crawford |
| 2014/0058406 A1 | 2/2014 | Tsekos |
| 2014/0107390 A1 | 4/2014 | Brown |
| 2014/0114180 A1 | 4/2014 | Jain |
| 2014/0142419 A1 | 5/2014 | Shalgi et al. |
| 2014/0142591 A1 | 5/2014 | Alvarez et al. |
| 2014/0148673 A1 | 5/2014 | Bogusky |
| 2014/0148808 A1 | 5/2014 | Inkpen et al. |
| 2014/0180063 A1 | 6/2014 | Zhao |
| 2014/0187915 A1 | 7/2014 | Yaroshenko et al. |
| 2014/0235943 A1 | 8/2014 | Paris |
| 2014/0243849 A1 | 8/2014 | Saglam |
| 2014/0257334 A1 | 9/2014 | Wong et al. |
| 2014/0257746 A1 | 9/2014 | Dunbar et al. |
| 2014/0264081 A1 | 9/2014 | Walker et al. |
| 2014/0275985 A1 | 9/2014 | Walker et al. |
| 2014/0275988 A1 | 9/2014 | Walker et al. |
| 2014/0276033 A1 | 9/2014 | Brannan |
| 2014/0276392 A1 | 9/2014 | Wong et al. |
| 2014/0276394 A1 | 9/2014 | Wong et al. |
| 2014/0276594 A1 | 9/2014 | Tanner et al. |
| 2014/0276646 A1 | 9/2014 | Wong et al. |
| 2014/0276934 A1 | 9/2014 | Balaji et al. |
| 2014/0276937 A1 | 9/2014 | Wong et al. |
| 2014/0277747 A1 | 9/2014 | Walker et al. |
| 2014/0296655 A1 | 10/2014 | Akhbardeh et al. |
| 2014/0309527 A1 | 10/2014 | Namati et al. |
| 2014/0309649 A1 | 10/2014 | Alvarez et al. |
| 2014/0343416 A1 | 11/2014 | Panescu |
| 2014/0350391 A1 | 11/2014 | Prisco et al. |
| 2014/0357953 A1 | 12/2014 | Roelle et al. |
| 2014/0357984 A1 | 12/2014 | Wallace et al. |
| 2014/0364739 A1 | 12/2014 | Liu |
| 2014/0364870 A1 | 12/2014 | Alvarez et al. |
| 2014/0379000 A1 | 12/2014 | Romo et al. |
| 2015/0051482 A1 | 2/2015 | Liu et al. |
| 2015/0051592 A1 | 2/2015 | Kintz |
| 2015/0054929 A1 | 2/2015 | Ito et al. |
| 2015/0057498 A1 | 2/2015 | Akimoto |
| 2015/0073266 A1 | 3/2015 | Brannan |
| 2015/0101442 A1 | 4/2015 | Romo |
| 2015/0112486 A1 | 4/2015 | Larkin et al. |
| 2015/0119638 A1 | 4/2015 | Yu et al. |
| 2015/0141808 A1 | 5/2015 | Elhawary et al. |
| 2015/0141858 A1 | 5/2015 | Razavi et al. |
| 2015/0142013 A1 | 5/2015 | Tanner et al. |
| 2015/0164594 A1 | 6/2015 | Romo et al. |
| 2015/0164596 A1 | 6/2015 | Romo |
| 2015/0223725 A1 | 8/2015 | Engel |
| 2015/0223765 A1 | 8/2015 | Chopra |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Park |
| 2015/0265359 A1 | 9/2015 | Camarillo |
| 2015/0265368 A1 | 9/2015 | Chopra |
| 2015/0265807 A1 | 9/2015 | Park et al. |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0297864 A1 | 10/2015 | Kokish et al. |
| 2015/0305650 A1 | 10/2015 | Hunter |
| 2015/0313503 A1 | 11/2015 | Seibel et al. |
| 2015/0335480 A1 | 11/2015 | Alvarez et al. |
| 2015/0374956 A1 | 12/2015 | Bogusky |
| 2015/0375399 A1 | 12/2015 | Chiu et al. |
| 2016/0000302 A1 | 1/2016 | Brown |
| 2016/0000414 A1 | 1/2016 | Brown |
| 2016/0000520 A1 | 1/2016 | Lachmanovich et al. |
| 2016/0001038 A1 | 1/2016 | Roma et al. |
| 2016/0008033 A1 | 1/2016 | Hawkins et al. |
| 2016/0111192 A1 | 4/2016 | Suzara |
| 2016/0128992 A1 | 5/2016 | Hudson |
| 2016/0175059 A1 | 6/2016 | Walker et al. |
| 2016/0183841 A1 | 6/2016 | Duindam et al. |
| 2016/0199134 A1 | 7/2016 | Brown et al. |
| 2016/0202053 A1 | 7/2016 | Walker et al. |
| 2016/0206389 A1 | 7/2016 | Miller |
| 2016/0213432 A1 | 7/2016 | Flexman |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0314710 A1 | 10/2016 | Jarc |
| 2016/0331469 A1 | 11/2016 | Hall et al. |
| 2016/0360947 A1 | 12/2016 | Iida et al. |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0055851 A1 | 3/2017 | Al-Ali |
| 2017/0065356 A1 | 3/2017 | Balaji et al. |
| 2017/0079725 A1 | 3/2017 | Hoffman |
| 2017/0079726 A1 | 3/2017 | Hoffman |
| 2017/0100084 A1 | 4/2017 | Walker et al. |
| 2017/0100199 A1 | 4/2017 | Yu et al. |
| 2017/0105803 A1 | 4/2017 | Wong et al. |
| 2017/0113019 A1 | 4/2017 | Wong et al. |
| 2017/0119413 A1 | 5/2017 | Roma |
| 2017/0119481 A1 | 5/2017 | Roma et al. |
| 2017/0119484 A1 | 5/2017 | Tanner et al. |
| 2017/0151027 A1 | 6/2017 | Walker et al. |
| 2017/0165011 A1 | 6/2017 | Bovay et al. |
| 2017/0172673 A1 | 6/2017 | Yu et al. |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0209224 A1 | 7/2017 | Walker et al. |
| 2017/0215808 A1 | 8/2017 | Shimol et al. |
| 2017/0215969 A1 | 8/2017 | Zhai et al. |
| 2017/0238807 A9 | 8/2017 | Vertikov |
| 2017/0258366 A1 | 9/2017 | Tupin |
| 2017/0290631 A1 | 10/2017 | Lee et al. |
| 2017/0296032 A1 | 10/2017 | Li |
| 2017/0296202 A1 | 10/2017 | Brown |
| 2017/0303941 A1 | 10/2017 | Eisner |
| 2017/0325896 A1 | 11/2017 | Donhowe |
| 2017/0333679 A1 | 11/2017 | Jiang |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360418 A1 | 12/2017 | Wong et al. |
| 2017/0360508 A1 | 12/2017 | Germain et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055582 A1 | 3/2018 | Krimsky |
| 2018/0098690 A1 | 4/2018 | Iwaki |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0184988 A1 | 7/2018 | Walker et al. |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289243 A1 | 10/2018 | Landey et al. |
| 2018/0289431 A1 | 10/2018 | Draper et al. |
| 2018/0308247 A1 | 10/2018 | Gupta |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |

(56) References Cited

U.S. PATENT DOCUMENTS

| | | |
|---|---|---|
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0046814 A1 | 2/2019 | Senden et al. |
| 2019/0066314 A1 | 2/2019 | Abhari |
| 2019/0083183 A1 | 3/2019 | Moll et al. |
| 2019/0086349 A1 | 3/2019 | Nelson |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0117176 A1 | 4/2019 | Walker et al. |
| 2019/0117203 A1 | 4/2019 | Wong et al. |
| 2019/0125164 A1 | 5/2019 | Roelle et al. |
| 2019/0151148 A1 | 5/2019 | Alvarez et al. |
| 2019/0167361 A1 | 6/2019 | Walker et al. |
| 2019/0167366 A1 | 6/2019 | Ummalaneni |
| 2019/0167367 A1 | 6/2019 | Walker et al. |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata et al. |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0155084 A1 | 5/2020 | Walker |
| 2020/0170630 A1 | 6/2020 | Wong |
| 2020/0170720 A1 | 6/2020 | Ummalaneni |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |

| | | |
|---|---|---|
| 2020/0261172 A1 | 8/2020 | Romo |
| 2020/0268459 A1 | 8/2020 | Noonan et al. |
| 2020/0268460 A1 | 8/2020 | Tse |
| 2023/0036116 A1 | 2/2023 | Walker et al. |

FOREIGN PATENT DOCUMENTS

| | | |
|---|---|---|
| CN | 102316817 A | 1/2012 |
| CN | 102458295 A | 5/2012 |
| CN | 102973317 A | 3/2013 |
| CN | 103735313 A | 4/2014 |
| CN | 104931059 A | 9/2015 |
| CN | 105559850 A | 5/2016 |
| CN | 105559886 A | 5/2016 |
| CN | 105611881 A | 5/2016 |
| CN | 106821498 A | 6/2017 |
| EP | 3025630 A1 | 6/2016 |
| JP | 2015-519131 A | 7/2015 |
| KR | 20140009359 A | 1/2014 |
| RU | 2569699 C2 | 11/2015 |
| WO | WO 2003/086190 A1 | 10/2003 |
| WO | WO 2005/087128 A1 | 9/2005 |
| WO | WO 2009/097461 A1 | 6/2007 |
| WO | WO 2013/116140 A1 | 8/2013 |
| WO | WO 2014/058838 A1 | 4/2014 |
| WO | WO 2015/089013 A1 | 6/2015 |
| WO | WO 2017/048194 A1 | 3/2017 |
| WO | WO 2017/066108 A1 | 4/2017 |
| WO | WO 2017/167754 A1 | 10/2017 |

OTHER PUBLICATIONS

Ciuti, Gastone, et al. "Intra-operative monocular 3D reconstruction for image-guided navigation in active locomotion capsule endoscopy." *2012 4th IEEE RAS & EMBS International Conference on Biomedical Robotics and Biomechatronics (BioRob)*. IEEE, 2012.

Fallavollita, Pascal. "Acquiring multiview c-arm images to assist cardiac ablation procedures." *EURASIP Journal on Image and Video Processing* 2010 (2010): 1-10.

Gutiérrez, Luis F., et al. "A practical global distortion correction method for an image intensifier-based x-ray fluoroscopy system." *Medical physics* 35.3 (2008): 997-1007.

Haigron, Pascal, et al. "Depth-map-based scene analysis for active navigation in virtual angioscopy." *IEEE Transactions on Medical Imaging* 23.11 (2004): 1380-1390.

Hansen Medical, Inc. 2005, System Overview, product brochure, 2 pp., dated as available at http://hansenmedical.com/system.aspx on Jul. 14, 2006 (accessed Jun. 25, 2019, using the internet archive way back machine).

Hansen Medical, Inc. Bibliography, product brochure, 1 p., dated as available at http://hansenmedical.com/bibliography.aspx on Jul. 14, 2006 (accessed Jun. 25, 2019, using the Internet archive way back machine).

Hansen Medical, Inc. dated 2007, Introducing the Sensei Robotic Catheter System, product brochure, 10 pp.

Hansen Medical, Inc. dated 2009, Sensei X Robotic Catheter System, product brochure, 5 pp.

Hansen Medical, Inc. Technology Advantages, product brochure, 1 p., dated as available at http://hansenmedical.com/advantages.aspx on Jul. 13, 2006 (accessed Jun. 25, 2019, using the internet archive way back machine).

Kiraly, Atilla P., et al. "Three-dimensional human airway segmentation methods for clinical virtual bronchoscopy." *Academic radiology* 9.10 (2002): 1153-1168.

Kiraly, Atilla P., et al. "Three-dimensional path planning for virtual bronchoscopy." *IEEE transactions on medical imaging* 23.11 (2004): 1365-1379.

Konen, W., M. Scholz, and S. Tombrock. "The VN project: endoscopic image processing for neurosurgery." *Computer Aided Surgery* 3.3 (1998): 144-148.

Kumar, Atul, et al. "Stereoscopic visualization of laparoscope image using depth information from 3D model." *Computer methods and programs in biomedicine* 113.3 (2014): 862-868.

(56) References Cited

OTHER PUBLICATIONS

Livatino, Salvatore, et al. "Stereoscopic visualization and 3-D technologies in medical endoscopic teleoperation." *IEEE Transactions on Industrial Electronics* 62.1 (2014): 525-535.

Luó, Xióngbião, et al. "Modified hybrid bronchoscope tracking based on sequential monte carlo sampler: Dynamic phantom validation." *Computer Vision—ACCV 2010: 10th Asian Conference on Computer Vision*, Queenstown, New Zealand, Nov. 8-12, 2010, Revised *Selected Papers, Part III 10*. Springer Berlin Heidelberg, 2011.

Marrouche, Nassir F., et al. "Preliminary human experience using a novel robotic catheter remote control." *Heart Rhythm* 2.5 (2005): S63.

Mayo Clinic, Robotic Surgery, https://www.mayoclinic.org/tests-procedures/robotic-surgery/about/pac-20394974?p=1, downloaded from the internet on Jul. 12, 2018, 2 pages.

Mourgues, Fabien, Eve Coste-Maniere, and CHIR Team www.inria. fr/chir. "Flexible calibration of actuated stereoscopic endoscope for overlay in robot assisted surgery." *International Conference on Medical Image Computing and Computer-Assisted Intervention*. Berlin, Heidelberg: Springer Berlin Heidelberg, 2002.

Nadeem, Saad, and Arie Kaufman. "Depth reconstruction and computer-aided polyp detection in optical colonoscopy video frames." *arXiv preprint arXiv:* 1609.01329 (2016).

Oh, Seil, et al. "Novel robotic catheter remote control system: safety and accuracy in delivering RF lesions in all 4 cardiac chambers." *Heart Rhythm* 2.5 (2005): S277-S278.

Point Cloud, Sep. 10, 2010, Wikipedia, 2 pages.

Racadio, John M., et al. "Live 3D guidance in the interventional radiology suite." *American Journal of Roentgenology* 189.6 (2007): W357-W364.

Reddy, Vivek Y., et al. "Porcine pulmonary vein ablation using a novel robotic catheter control system and real-time integration of CT imaging with electroanatomical mapping." *Heart Rhythm* 2.5 (2005): S121.

Sato, Masaaki, Tomonori Murayama, and Jun Nakajima. "Techniques of stapler-based navigational thoracoscopic segmentectomy using virtual assisted lung mapping (VAL-MAP)." *Journal of thoracic disease* 8.Suppl 9 (2016): S716.

Shen, Mali, Stamatia Giannarou, and Guang-Zhong Yang. "Robust camera localisation with depth reconstruction for bronchoscopic navigation." International journal of computer assisted radiology and surgery 10 (2015): 801-813.

Shi, Chaoyang, et al. "Simultaneous catheter and environment modeling for trans-catheter aortic valve implantation." *2014 IEEE/ RSJ International Conference on Intelligent Robots and Systems*. IEEE, 2014.

Slepian, dated 2010, Robotic Catheter Intervention: the Hansen Medical Sensei Robot Catheter System, PowerPoint presentation, 28 pages.

Solheim, Ole, et al. "Navigated resection of giant intracranial meningiomas based on intraoperative 3D ultrasound." *Acta neurochirurgica* 151 (2009): 1143-1151.

Solomon, Stephen B., et al. "Three-dimensional CT-guided bronchoscopy with a real-time electromagnetic position sensor: a comparison of two image registration methods." *Chest* 118.6 (2000): 1783-1787.

Song, Kai-Tai, and Chun-Ju Chen. "Autonomous and stable tracking of endoscope instrument tools with monocular camera." *2012 IEEE/ASME International Conference on Advanced Intelligent Mechatronics (AIM)*. IEEE, 2012.

Vemuri, Anant Suraj, et al. "Interoperative biopsy site relocalization in endoluminal surgery." *IEEE Transactions on Biomedical Engineering* 63.9 (2015): 1862-1873.

Verdaasdonk, R. "Effect of microsecond pulse length and tip shape on explosive bubble formation of 2.78 µm Er, Cr; YSGG and 2.94 µm Er: YAG laser." *Proceedings of SPIE*. vol. 8221. No. 12. 2012.

Wilson, Emmanuel, et al. "A buyer's guide to electromagnetic tracking systems for clinical applications." *Medical Imaging 2008: Visualization, Image-Guided Procedures, and Modeling*. vol. 6918. SPIE, 2008.

Yip, Michael C., et al. "Tissue tracking and registration for image-guided surgery." *IEEE transactions on medical imaging* 31.11 (2012): 2169-2182.

Zhou, Jin, et al. "Synthesis of stereoscopic views from monocular endoscopic videos." *2010 IEEE Computer Society Conference on Computer Vision and Pattern Recognition-Workshops*. IEEE, 2010.

1

FLEXIBLE INSTRUMENT LOCALIZATION FROM BOTH REMOTE AND ELONGATION SENSORS

This application is a continuation of U.S. patent application Ser. No. 17/881,759, entitled "Flexible Instrument Localization from Both Remote and Elongation Sensors," filed Aug. 5, 2022, published as U.S. Pub. No. 2023/0036116 on Feb. 2, 2023 and issued as U.S. Pat. No. 12,016,669 on Jun. 25, 2024; which is a continuation of U.S. patent application Ser. No. 15/056,652, entitled "Flexible Instrument Localization from Both Remote and Elongation Sensors," filed Feb. 29, 2016, issued as U.S. Pat. No. 11,426,095 on Aug. 30, 2022; which is a continuation of U.S. patent application Ser. No. 13/833,733, entitled "Flexible Instrument Localization from Both Remote and Elongation Sensors," filed Mar. 15, 2013, issued as U.S. Pat. No. 9,271,663 on Mar. 1, 2016.

TECHNICAL FIELD

The proposed disclosure utilizes techniques to determine the location, orientation, and shape of a flexible device by utilizing remote localization techniques (such as fluoroscopy, electromagnetic sensors, etc.) with elongation measurements (such as drive wire displacements, tendon tension, etc.) to produce effective localization of the flexible device in a target coordinate frame.

BACKGROUND

Currently known minimally invasive procedures for diagnosis and treatment of medical conditions use shapeable instruments, such as steerable devices, flexible catheters or more rigid arms or shafts, to approach and address various tissue structures within the body. For various reasons, it is highly valuable to be able to determine the 3-dimensional spatial position of portions of such shapeable instruments relative to other structures, such as the operating table, other instruments, or pertinent anatomical tissue structures. Such information can be used for a variety of reasons, including, but not limited to: improve device control; to improve mapping of the region; to adapt control system parameters (whether kinematic and/or solid mechanic parameters); to estimate, plan and/or control reaction forces of the device upon the anatomy; and/or to even monitor the system characteristics for determination of mechanical problems. Alternatively, or in combination, shape information can be useful to simply visualize the tool with respect to the anatomy or other regions whether real or virtual.

However, a primary difficulty in using flexible devices is the inability to determine the location and/or shape of the flexible device within the body. In non-flexible, discrete devices, such detection and monitoring tasks may be accomplished with encoders or other techniques (such as visual tracking of a portion of the device external to the body) that utilized the rigid nature of linkages. Such conventional techniques are not practical with flexible device as such devices contain non-rigid linkages or too many individual linkages to effectively determine location and/or shape of the flexible device.

There remains a need to apply the information gained by the localization techniques to determine the location, orientation and shape of a flexible device and applying this information to produce improved device control or improved modeling when directing a robotic or similar device. There also remains a need to apply such controls to medical procedures and equipment.

SUMMARY

A system and method of tracking a flexible elongate instrument within a patient is disclosed herein. The system is configured to obtain remote localization measurement data of the flexible elongate instrument and obtain elongation measurement data of the flexible elongate instrument. This data is combined and transformed to a coordinate reference frame to produce a localization of the flexible elongate instrument that is more accurate than the remote localization measurements or elongation alone. The combined localization is then provided to a localization consumer.

DETAILED DESCRIPTION OF THE INVENTION

Overview of Flexible Device Localization

Figure 1:
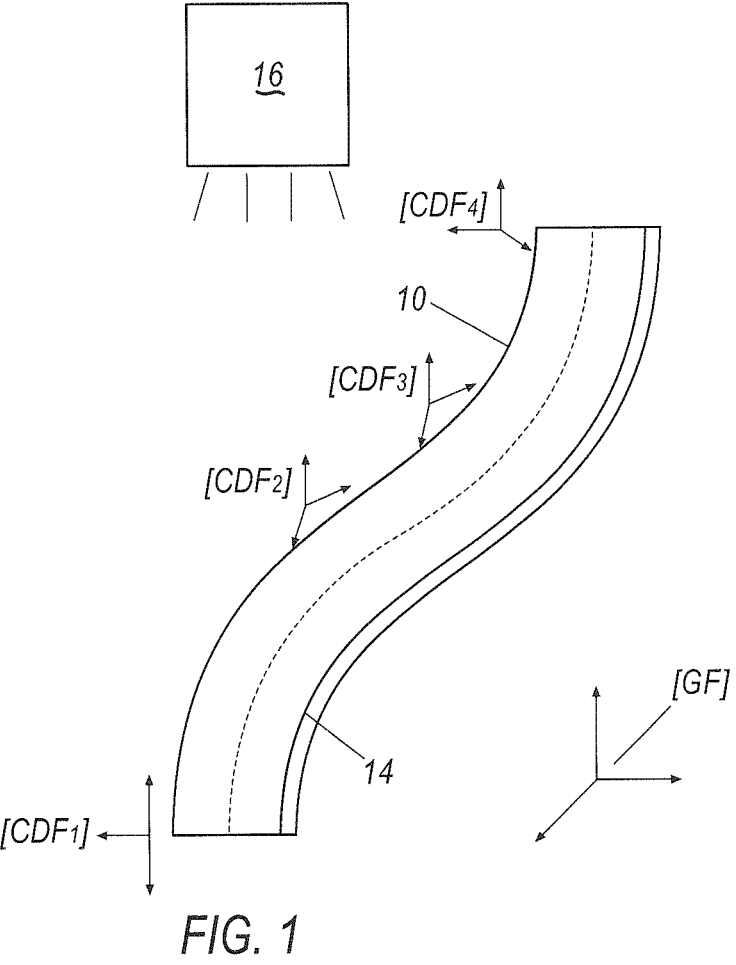
FIG. 1 is an illustration of various coordinate frames of an elongation element and a global reference frame.

With reference to FIG. 1, localization of a flexible device 10 will be described. Localization of a flexible device is determining a mapping from one or more device coordinate frames for a flexible device 10 to a global target frame. More specifically, the flexible device 10 of FIG. 1 is defined in terms of localization by one or more Cartesian device reference frames, such as, for example, coordinate frames CDF1, CDF2, CDF3, CDF4. These reference frames are typically defined by three-dimensions of position and three dimensions of orientation. Thus, the goal of localization is to determine the relationship, or mapping between the local device reference frames (i.e., CDF1, CDF2, CDF3, CDF4) and a fixed, global or target reference frame GF in relation to the task to be performed. The mapping is performed using a combination of one or more remote localization measurements LM (which will be referenced to the global reference frame) and an elongation measurement EM (which will be referenced to the device itself).

An exemplary technique of utilizing a remote localization measurement with elongation measurements are particularly useful when the remote localization measurements are insufficient to fully describe the position, orientation, and shape of the flexible device (i.e., mapping for each device reference frame) or remote localization measurements are not accurate enough as a standalone localization technique.

Figure 2:
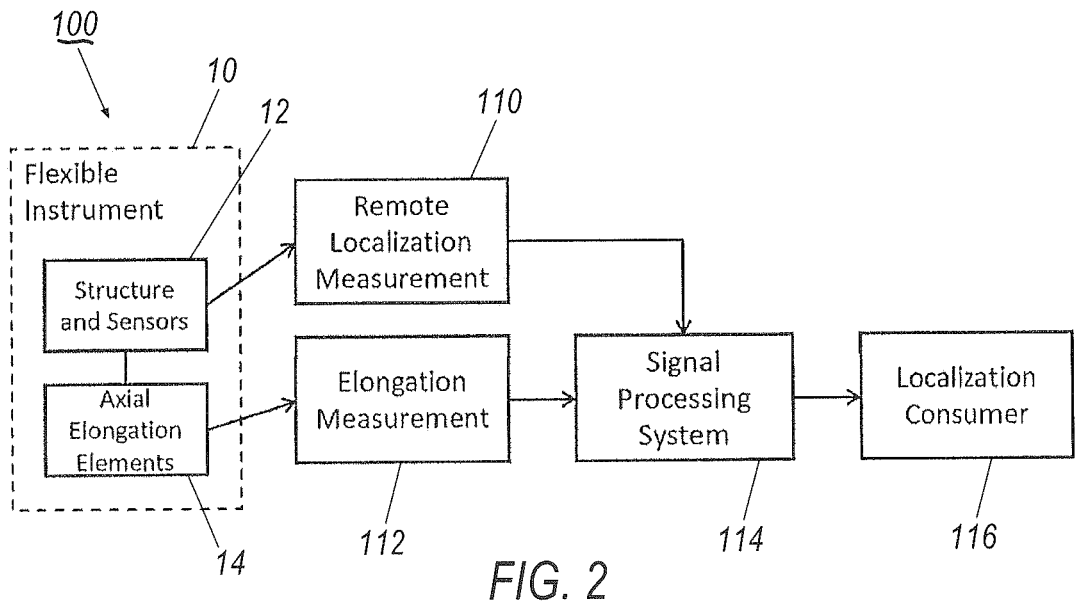
FIG. 2 is a schematic illustration of a system for localization of a flexible instrument using a remote localization measurement and an elongation measurement.

The basic structure for the proposed localization technique 100 is illustrated in FIG. 2. The proposed localization technique 100 utilizes both remote localization measurements 110 and elongation measurements 112. Elements of technique 100 are discussed in further detail below.

The flexible device 10 may be any device that contains continuously articulating joints (including, but not limited to, a manual catheter, robot catheter, etc.). Alternatively, the flexible device 10 may be configured as a device that includes a substantial number of rigid linkages that makes modeling kinematics of the device 10 difficult and unmanageable. The device 10 may include one more sensors 12. The device 10 may also include one or more elongation elements 14. Sensors 12 and elongation elements 14 will be described below in further detail.

A remote localization device is any signal from a sensor 12 that is positioned outside of the flexible device 10 that is registered to the global reference frame GRF. An example of a remote localization device is a fluoroscopy system 16, shown in FIG. 1. The fluoroscopy view provides the shape and location of flexible device 10, although certain information, such as depth, cannot be measured. The remote localization device can accurately sense the shape of the flexible device 10, usually through the use of markers or sensors mounted on the flexible device 10, as well as sensing the flexible device 10 in relation to a reference frame outside of the flexible device 10. Various technologies that may be used for remote localization are discussed in further detail below.

As depicted in the schematic of FIG. 1, an elongation element 14 is an axially disposed element located within the flexible device 10. Elongation element 14 may take various forms, but its primary purpose is to measure differences in an axial path length APL between a reference path RP within the flexible device 10. In one exemplary configuration, the reference path RP is a center axis of the flexible device 10 and a secondary path is positioned off the center axis. One exemplary configuration of an elongation element 14 is a tendon that may be used to articulate the flexible device 10. However, it is understood that any element that allows a differential measurement between two axial paths of the flexible device 10 may be used to calculate an elongation measurement. The primary use of the differential measurement from an elongation element is to determine the approximate shape and heading of the flexible device 10.

It is also understood that an elongation measurement is not limited to displacement measurements from stretching. Alternatively, elongation measurements such as compression, tension in an element fixed at either the proximal or distal end of the flexible device 10, or displacement of fluid in a tube may be used. Elongations measurements are discussed in further detail below.

Because the information gleaned from the sensors 12 and the elongation elements 14 are disparate streams of data, a signal processing system 114 that can combine the two data streams into a single localization signal is proposed. There are a variety of methods that may be used with the signal processing system 114. However, a primary element of the signal processing system 114 is a method of representing the possible shapes of the device in the global reference frame and using sensor information to reduce the number of possibilities. Filters, estimation, and modeling are suitable techniques for accomplishing effective mapping between position and orientation of multiple points on the device and the global reference frame GRF. In addition, commands for a flexible robot may be incorporated into the signal processing system to increase accuracy.

The signal processing system 114 is coupled to a localization consumer 116. The localization consumer 116 is the eventual user of the relationship between the flexible device 10 and the global reference frame GRF. Non-limiting examples include a robot control system, a sensing system for recording a surgical procedure, or a graphical display utilized by a human operator.

Remote Localization Overview

As discussed above, a number of technologies may be used to determine the shape and position of a flexible device 10 with respect to a fixed reference frame GRF using sensors 12. In the context of medical devices, including, but not limited to medical catheters, the reference frame may be defined by a part of the patient's anatomy, the table upon which the patient lies, or the world. Complete configuration of a rigid three-dimensional object may be specified by six degrees of freedom. These degrees of freedom are described by three positional coordinates (e.g., the x, y, and z coordinates of a Cartesian frame) and three rotational coordinates (e.g., roll, pitch, and yaw).

Depending on which type, and the number of sensors 12, a localization system may measure the configuration of a flexible device 10 with respect to all six degrees of freedom, or a subset thereof. For example, a 2 dimensional sensor may determine the position of a given point on the flexible device 10 as projected onto a fixed plane. A 3 dimensional sensor may determine the complete 3D position of a given point on a flexible device 10, but not the rotation of the flexible device 10. A 2 degrees of freedom directional sensor may measure the heading direction (pitch and yaw) of the flexible device 10, but not its roll about that axis. A five degrees of freedom sensor may measure both the position and heading of an object. A five degrees of freedom localization system can constructed from two 3D positional sensors, with the heading direction determined by the vector between them. In a sufficiently constrained anatomy, a 3 degrees of freedom position sensor may be combined with a 3D map (generated from a preoperative imaging scan, such as a CT scan), registered to the same reference frame as the sensor, in order to estimate the heading direction of flexible device 10 (modulo a 180 degree rotation) under the assumption that the flexible device 10 must be in the direction allowed locally by the anatomical map. A six degrees of freedom sensor may full specify the position, roll, pitch, and yaw of the flexible device 10.

Figure 3:
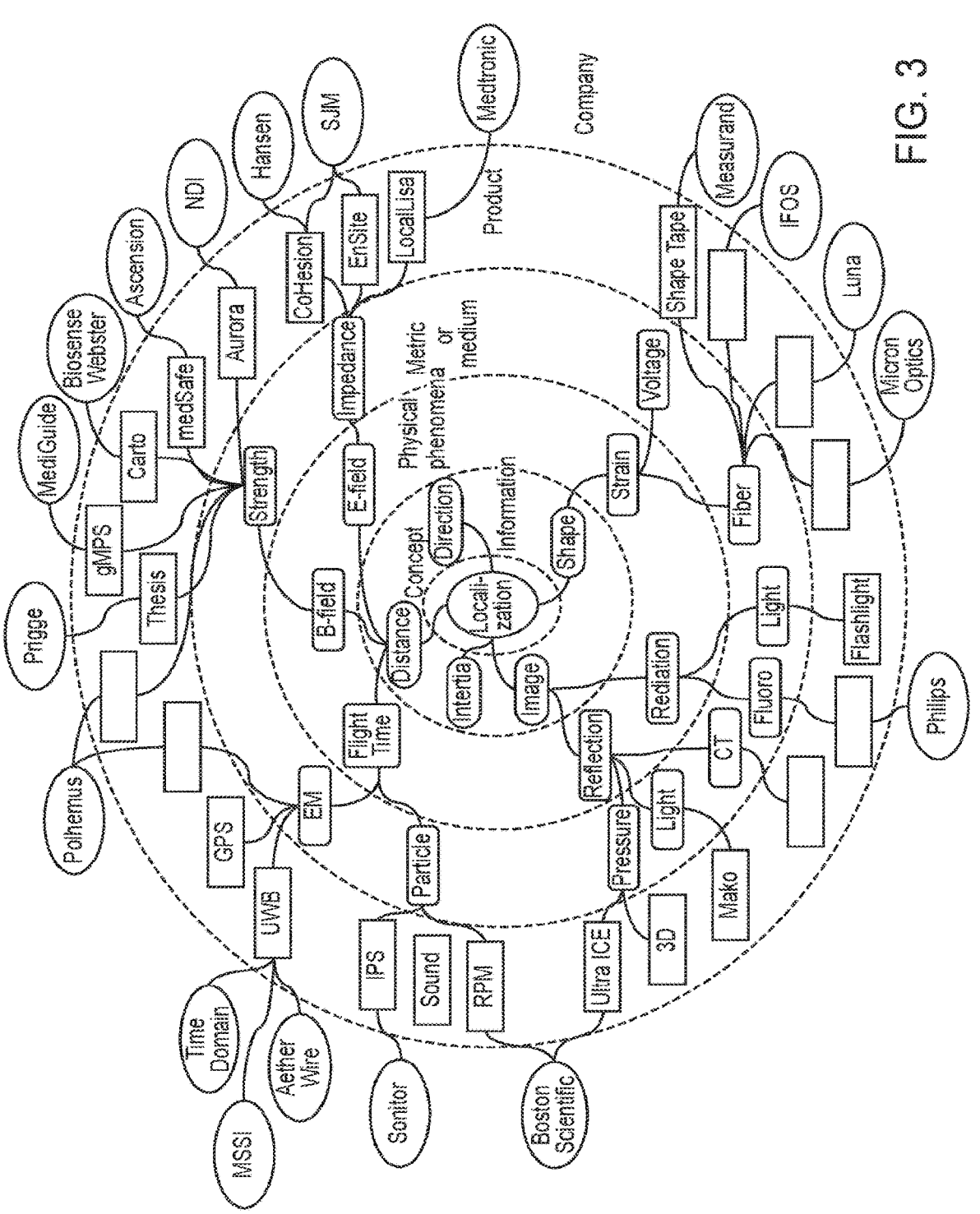
FIG. 3 is a map of remote localization technologies.

As demonstrated in FIG. 3, a variety of physical phenomena may form the basis for a localization system. Many systems operate by determining a distance of one or more sensors from reference locations and triangulating a position based on that data. For example, some systems determine the distance by measuring impedance of an electric field. In one known system, electrodes on a flexible catheter and a plurality electrical patches placed on the patient's body are used to compute the 3D position of at least two electrodes, thereby resolving five degrees of freedom. In another known system, six degrees of freedom are resolved by using magnets and a sensor that measures the strength of the magnetic field. In still another known system, time-of-flight waves between emitters and receivers are measured. For example, for GPS, radio waves may be used. In ultra-sound based systems, pressure waves may be used.

An imaging system (such as a fluoroscopy system 16) may also be used to localize a flexible device 10 with respect to its camera frame when coupled with an algorithm that can detect one or more specified points of the flexible device 10 within the image. Certain imageable materials (such as radio-opaque markers) may be used to enable the specified points to stand out on the image. If only a single point is tracked by the algorithm, a 2D position of the object as projected onto the imaging plane may be determined. If two points are tracked, one rotational degree of freedom may also be computed. More specifically, the heading direction as projected onto the imaging plane may be determined. The distance between the two points, distinct texturing of the markers, and/or simultaneous imaging and tracking in another image plane can be used to determine the heading direction in or out of the original imaging plane. The simultaneously imaging and tracking in different planes may also be used to resolve the third positional coordinate. Further, distinctive texturing of the markers may also be used to estimate the final rotational degree of freedom, i.e., roll.

While remote localization sensors may aide in determining some information about the location of a flexible device 10 disposed within a body, often the sensors are unable to capture important information. For example, as discussed above, a fluoroscopy image is usually a single, planar projection. Thus depth information is not present. As another example, coil electromagnetic sensors disposed within the flexible device may not be able to sense roll about a principal axis. Thus, a supplemental source of information to compliment the information obtainable by remote localization sensors may lead to greater accuracy in localization.

Elongation Measurements Overview

As illustrated in FIG. 2, information about deformation of a flexible device 10, which may be obtained from elongation sensors, may be used to supplement information obtained by remote localization sensors. The deformation information may be transmitted for the length of the flexible device 10 by a member that may be configured to elongate or contract based on its relative placement to the centroid of the flexible device 10 as the flexible device 10 articulates.

Figures 4A, 4B, 5:
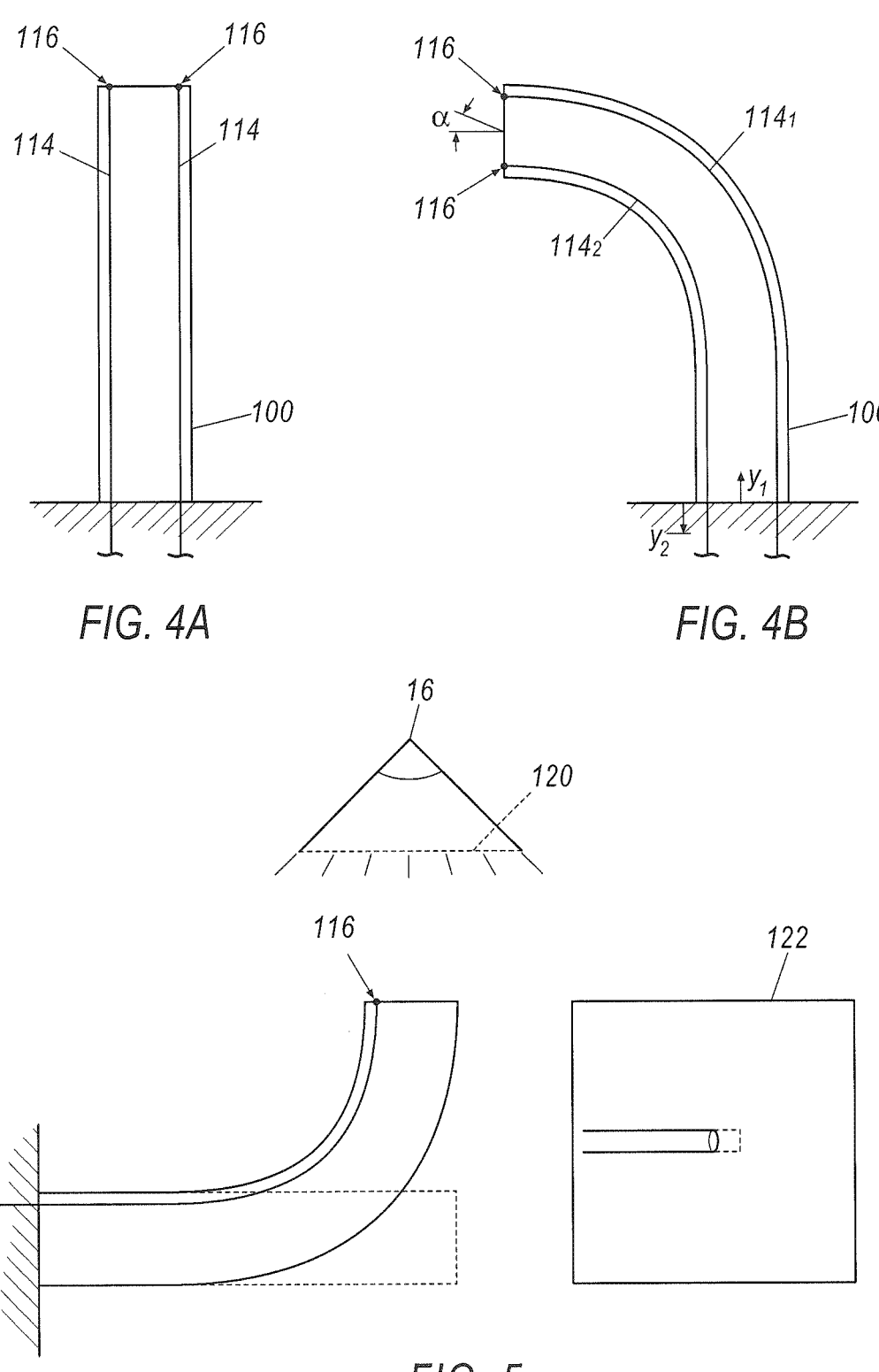
FIG. 4A is an illustration of a flexible device with actuation elements terminated distally, in an unarticulated configuration.
FIG. 4B is an illustration of the flexible device of FIG. 4A in an articulated configuration.
FIG. 5 is a schematic illustration of the flexible device of FIG. 4B with respect to an imaging plane.

In a catheter, for example, one exemplary source of elongation information would be actuation elements 14 that move to selectively articulate the catheter. Referring to FIGS. 4A-4B, a catheter 100 includes at least a pair of tendons 114 that each include a first end 116 that is terminated distally. As the first end 116 is displaced proximally, illustrated in FIG. 4B, a distal motion results. Thus, for the catheter 100 to bend, the material at the circumference of the catheter 100 must either elongate or compress. The motion of the tendon 114 gives an indication of the degree of elongation, and therefore the extent of the articulation. This information can assist in predicting the location and/or orientation of the catheter 100 within the body, especially if the bending motion flexible device 10 is out of a fluoroscopy plane, as illustrated in FIG. 5. Indeed, as may be seen in FIG. 5, for a catheter motion out of the fluoroscopy plane 120, only a small catheter tip motion will be observed on an image panel 122 as the bulk of the motion is toward the fluoroscopy plane 120.

In the case of a catheter 100 being oriented in a straight line within a patient, the pitch and yaw angles of the catheter 100 can be related linearly to the tendon 114 displacements, as represented by the following formula:

$$\propto \, = f(y1,\, y2). \hspace{2cm} [1]$$

For more complicated anatomy where the catheter 100 will curve and twist, external remote localization may assist with a global reference frame GRF, whereas elongation measurement may be desirable for local differential measurements.

Displacement of a tendon 114 may be indicative of elongation on the circumference of the catheter 100. However there may be some components that must be compensated for. As a non-limiting example, if the tendon 114 is under load and stretches, an indication of its force may be used to remove its own strain. Similarly, the total force on the catheter 100 may indicate compression of the catheter 100 that must be compensated for since the differential elongation of the catheter 100 from one side to the other side is the quantity of interest. If multiple tendons 114 are used, their respective differential displacement information may be sufficient to indicate orientation.

Although tendons 114 are one example as a source of elongation information, there are other potential sources that are contemplated by the present discussion. One non-limiting example includes an electrical lead that may be routed circumferentially, but configured to float within a lumen. The electrical lead may be used for obtaining elongation information as it displaces.

Instrument channels may also provide a mechanism for measuring elongation if such channels are positioned off center of the flexible device 10. In one exemplary configuration, the instrument channel is fixed distally. In another exemplary configuration, instrument channel is fixed proximally and measured distally by either internal or external sensing. In yet another exemplary configuration, instrument channel may be fixed at either end, elongation is measured at both the distal and proximal ends.

In yet another exemplary configuration, a pressure filled circumferential lumen may be utilized. More specifically the lumen is filled with either gas or fluid which may be used to generate signals as the pressure and/or displaced volume changes with articulation. Further, the pressure filled lumens may also be used to exert positive pressure or negative pressure to articulate the flexible device 10.

In a further exemplary configuration, pushrods may be utilized. More specifically, pushrods may be pushed or pulled to articulate the flexible member. Displacement/force may be measured to estimate circumferential elongation on the flexible device.

When using a tension element, such as a cable, use of a Bowden Coil (also known as a coil tube) that can support the tension distally and decouple the flexible shaft motion from tendon actuation may be useful. The Bowden Coil itself could then be measured for device elongation information, as the Bowden Coil must displace back and forth as the device shaft is articulated. However, the Bowden Coil is most likely to be under significant load and therefore compress during articulation. Thus, the load should be estimated and compensated for in calculating the device elongation.

The Bowden Cable may be used in tandem with a tendon 114. The elongation measurement from the Bowden Coil may give articulation information at a point along the length of flexible where the Bowden Cables are terminated, and the tendons may provide articulation information about the segment distal to the Bowden Coil termination.

In another exemplary arrangement, a fiber optic line may be used to deliver energy or estimate shape/strain of a flexible device 10. The proximal motion of the fiber optic line, if fixed distally, would indicate circumferential elongation of the flexible device 10.

Elongation information of interest is at specific known locations about the circumference of the flexible device 10. However, elongation at multiple points about the circumference of the flexible device 10 provides value since differential elongation provides an indication of device articulation. Thus in one exemplary arrangement, a plurality of elongate elements may be disposed about the circumference to improve knowledge about the elongation of the flexible device 10. In one exemplary configuration, the plurality of elongate elements may all be terminated at the distal tip of the flexible device 10 to give fine articulation information. In another exemplary arrangement, the plurality of elongate elements may be terminated (or simply measured) at multiple points along the length of the flexible device 10 to give more complete shape information. Once such exemplary configuration is described above; i.e., utilizing the Bowden Coil with tendons, in which two points along the length of the catheter will generate articulation information. A continuous strain measuring instrument could be embedded and fixed in the flexible device that would provide elongation information at multiple points along the length of the flexible device. If a plurality of these strain measurements are routed in parallel on the length of the flexible device 10, the differential measurements could provide complete articulation information about any point along the length of the flexible device.

Motion Based Orientation Registration

Figure 6:
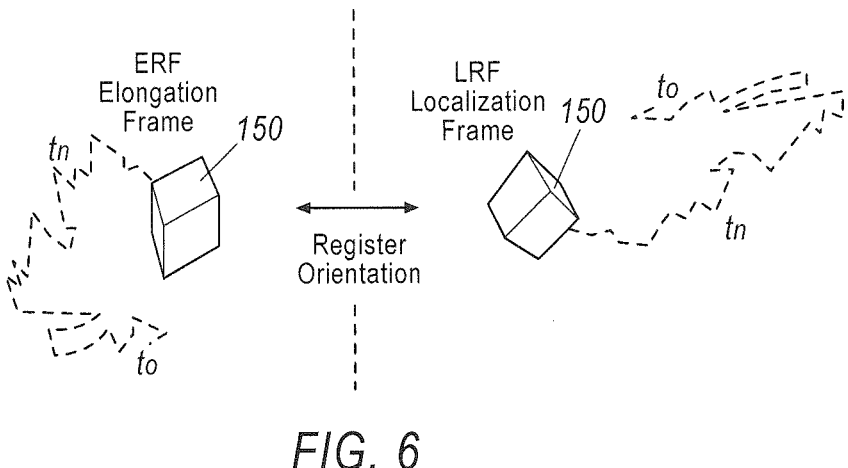
FIG. 6 illustrates how separate orientation frames may be registered to each other by correlating motion of a common object in each.

The remote localization measurement and elongation time history data are useful for registering to orientation in a localization frame, such as global reference frame GRF. FIG. 6 illustrates two views of an object 150 in motion in a pair of reference frames, an elongation reference frame ERF and a localization reference frame LRF. Correlating each measured motion in time allows a combination of the signals and improvement of a localization estimate. For example, separate orientation frames may be registered to each other by correlating motion of a common object in each frame. In certain exemplary arrangements that actuate a flexible device, a rich, but low amplitude identification signal may be embedded in an actuation command to aid in the correlation.

If two reference frames are not registered in orientation, objects appearing in each reference frame will be interpreted as rotated differently to an observer of both, such as shown in FIG. 6. Rotation values for each translational degree of freedom are thus required to register the elongation reference frame ERF and the localization reference frame LRF.

Thus, to register the orientation, the signal processing system 114 illustrated in FIG. 2 translates elongation measurements 112 into an expected motion in the elongation reference frame ERF of those measurements. Next, the signal processing system 114 determines the orientation (rotation angles) which will best match the expected motion to motion that is measured by the remote localization system 110. This determination may be accomplished by analyzing the time history of measurements (to infer motion), or by keeping an estimate of the state of the system and updating the estimate based on new measurements. In one exemplary configuration, a level of uncertainty of some states may be accounted for by a Kalman filter.

While the above proposed technique does not register position, in some instances orientation is sufficient for a control system to register its commands to an operator selected reference frame. With certain systems, the proposed orientation registration technique may be able to also register positions over time if the two localization data streams include position measurements. Such systems will require correspondingly more data measurements to register the extra degrees of freedom.

Exemplary configurations of the proposed orientation registration technique are described below. In a first exemplary configuration, a 5 degree of freedom measurement is combined with motion of flexible device 100 with four pullwires actuating near a point of measurement with a proximally measured position. In a second exemplary configuration, the same flexible device 100 with the four pullwires is combined with a 2 degree of freedom fluoroscopic measurement of a projected motion. Each will be discussed in turn.

First Exemplary Configuration

Figure 7:
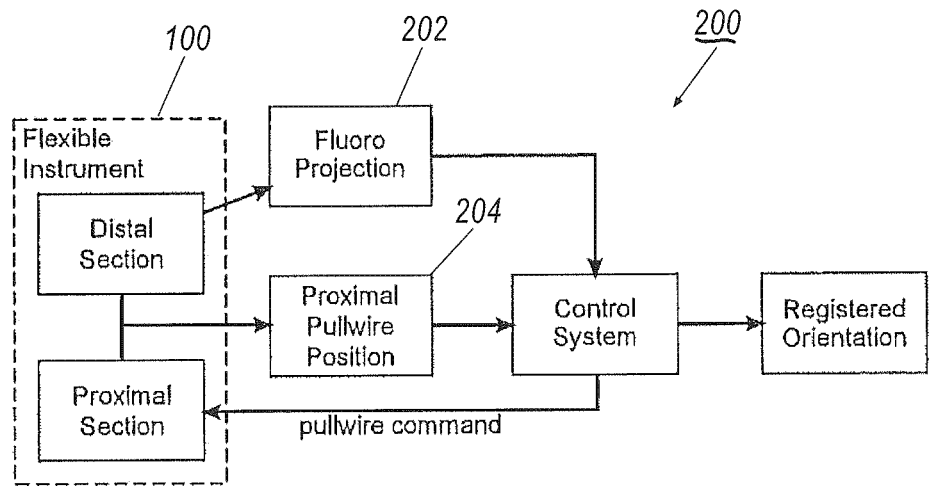
FIG. 7 is a schematic illustration of a system for localization of a flexible instrument using data from a 5 degrees of freedom electromagnetic sensor with measured pullwire position data.

Known five degrees of freedom remote localization systems 200 that are marketed for medical use do not measure the roll of a flexible device 100. However, roll may be estimated by combining a 5 degree of freedom measurement taken from an electromagnetic sensor 202 with measured pullwire positions 204 in the presence of a multi-dimensional motion path, as illustrated in FIG. 7. The flexible device 100 may be moved with the pullwires to follow a path so as to involve multiple pullwires. In one example, the path is a circle. During this movement, the time history of the pullwire positions and the remote localization measurements may be captured. The localization measurements are recorded as a matrix y. The pullwires positions are translated into the expected motion path, x, with a roll of zero. A roll matrix A, in the registered frame around the y-axis will translate x into the reference frame of y.

$$A(\theta) = \begin{bmatrix} \cos(\theta) & 0 & \sin(\theta) \\ 0 & 1 & 0 \\ -\sin(\theta) & 0 & \cos(\theta) \end{bmatrix} \quad (1)$$

The roll will satisfy the optimization as follows:

$$\underset{\theta}{\text{minimize}} \; \|y - A(\theta)x\|_2^2. \quad (2)$$

In another exemplary configuration, the roll optimization may be formulated as a state-update estimation.

Second Exemplary Configuration

Figure 8:
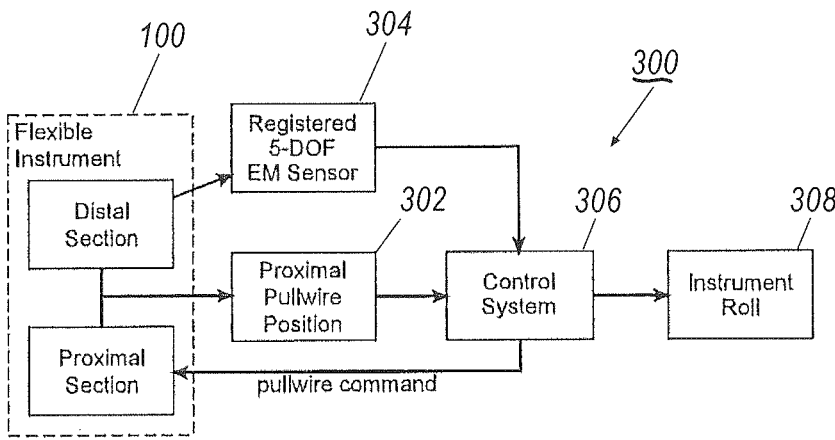
FIG. 8 is a schematic illustration of a system for localization of a flexible instrument using fluoroscopy imaging data with measured pullwire position data.

A second exemplary configuration 300 is illustrated schematically in FIG. 8. In this proposed technique, registration of flexible device 100 is accomplished by using position data 302 from an actuated pullwire device moving in three dimensions with a projected motion measured in two dimensions 304. All three rotation angles must be estimated to register orientation of the flexible device 100. A control system 306 combines the position data 302 from the pullwires with the position data 304 from the fluoroscopy system to register 308 an orientation of the device 100.

As with the first exemplary configuration discussed above, the pullwire motions are translated to expected device motions. The expected device motions in this exemplary configuration is projected onto a fluoroscopy plane 304. The pullwires further have a very small amount of motion overlaid constantly.

This technique begins by first assuming that the pullwires lie at a cardinal angel positions, $\lambda$. $\lambda$ is represented by the following:

$$\lambda = \left[0, \frac{\pi}{2}, \pi, \frac{3\pi}{2}\right] \qquad (3)$$

Next, a rotation matrix for motion in the plane 304 is determined:

$$P(\psi) = \begin{bmatrix} \cos(\psi) & -\sin(\psi) \\ \sin(\psi) & \cos(\psi) \end{bmatrix} \qquad (4)$$

In the rotation matrix, $\psi$ represents the yaw in the fluoroscopy reference frame 304. The expected motion is calculated as follows:

$$A(\phi, \theta) = \begin{bmatrix} \sin(\lambda - \phi) & 0 \\ \sin\left(\lambda - \phi - \frac{\pi}{2}\right)\sin(\theta) & \cos(\theta) \end{bmatrix} \qquad (5)$$

Where $\phi$ and $\Theta$ represents roll, both in the fluoroscopy reference frame 304. The transformation matrix to apply to motion in each tendon and insert axis is as follows:

$$B(\psi,\phi,\theta)=P(\psi)A(\phi,\theta)$$

Where $B \in IR2x5$

Small motions may be created and measured using the elongation tendons. Such motions should be translated into motion in a Cartesian direction at the distal section, such as, for example:

$$x = \begin{bmatrix} 1 & 0 & 0 & 0 & 0 & 1 \\ 0 & 0 & 1 & 1 & 0 & 0 \\ 0 & 1 & 0 & 0 & 0 & 1 \\ 0 & 0 & 0 & 0 & 1 & 0 \\ 0 & 0 & 1 & 1 & 0 & 1 \end{bmatrix} \ldots \qquad (7)$$

Where the columns in the above matrix each represent a time step and each row represents a direction to be projected onto the measurement plane. $x \in IR^{5xN}$, for N time samples. Here x(1) is a sideways motion of the tip caused by actuation of a single tendon.

The measurements in the fluoroscopy plane $y \in IR^{Nx2}$, represent two-dimensional motion over the same time-steps used for input matrix. However, mechanical systems have bandwidth limitations such that time steps will be much slower than the sampling rate of system electronics—1 to 10 Hz.

Finally, the difference between the time histories of the estimated motion projection and the fluoroscopy measurement should be minimized by properly selecting the rotation angles, as represented by the below formula:

$$\underset{\psi,\phi,\theta}{\text{minimize}} \; \|y - B(\psi, \phi, \theta)x\|_2^2. \qquad (8)$$

With constraints on $\omega$, $\phi$, and $\theta$, the minimization performed by the control system 306 will reveal the proper orientation to register the flexible device frame (i.e., through the use of the proximal pullwire position 302) to the fluoroscopy frame (through the use of the fluoroscopy projection 304). In another exemplary configuration, the orientation may be formulated as a state-update estimation.

It is understood that the present disclosure is not limited to the first and second exemplary configuration described above. Indeed, other combinations of motion measured via a remote localization system and elongation measurements may be combined with a signal processing system to register orientation in an elongation reference frame to the localization reference frame and improve localization.

Combining Remote Localization and Elongation Measurement

There are a number of different techniques that may be used to combine remote localization data and elongation data to register a tool or surgical device 100 to a target frame. Several exemplary techniques will now be discussed in turn.

Localization with Fluoroscopy and Elongation Measurements

There are a number of imaging techniques that may be used to project a 3D view of a flexible medical device, such as flexible device 100, to a 2D planar view. One commonly known and used technique is fluoroscopy, although the techniques presented herein may also be used with any camera view, including visible light and unobstructed views. For ease of explanation, the exemplary proposed technique will be described in the context of a fluoroscopy.

Figure 9:
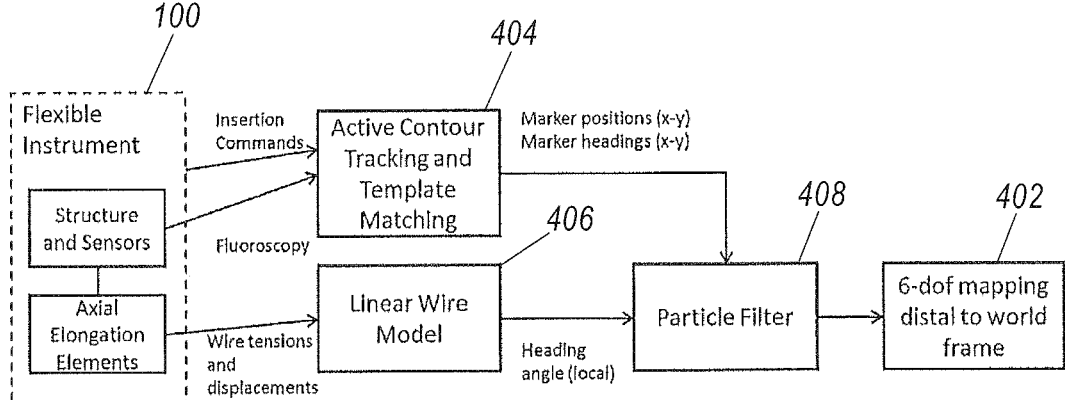
FIG. 9 is a schematic illustration of a system for localization of a flexible instrument using active contour tracking and template matching with linear wire model data.

With reference to FIG. 9, there are three main elements to a system 400 that augments an imaging technique with elongation measurements to register a flexible device 100 to a target frame 402. A first element is computer vision techniques that track the flexible device 100 within a fluoroscopy view to produce a computer vision model 404. While it is understood that there are many ways to track the flexible device 100, the primary goal is to process an image (and optionally, device commands) and prior information about the flexible device 100 to produce two-dimensional estimations of the position and heading of known positions on the flexible device 100. A second element of the system 400 is a model of the elongation elements 406, such as, for example, control wires, that are used to process tension and/or displacement information so as to estimate a heading and position. A third element of the system 400 is a signal processing element 408 that combines information from the computer vision model 404 and the linear wire model 406 to produce six degrees of freedom that maps the end of the flexible device 100 to coordinate frames of a proximal portion of the flexible device 100, and an imaging frame. Each element of the system 400 will be discussed below in further detail.

Computer Vision Technique

A primary goal of computer vision technique for remote localization measurement is to obtain estimates of distinguishable features on the flexible device 100 with a coordinate frame of an imaging device. In most known surgical suite setups, the imaging device coordinate frame is registered within the global frame GF, so once the flexible device 100 is localized or registered to the imaging device coordinate frame, it may effectively be registered within the global frame GF.

However, the localization from an imaging device is limited to two dimensions, as the images are two dimensional. More specifically, the position of each distinguishable feature of the flexible device 100 is typically represented as two-dimensional and with an unknown depth. Moreover, orientation from the imaging system may only provide a single degree of freedom—i.e., orientation angel within the plane. Thus, localization from an image gives no indication of the orientation in and out of the plan. Nor is roll around an axis of the flexible device 100 represented. Orientation and roll information can provide valuable information to effect proper localization and registration of a flexible medical device 100 within a target frame.

Tracking multiple features on a flexible device can improve depth and orientation estimates if the distances between each of the features are known. In typical 3D object tracking with computer vision techniques, all six degrees of freedom may be determined using the multiple features, as well as knowledge about occlusions. Thus, for flexible devices 100, it is possible to estimate the displacement of two reference points in or out of the imaging plane, but not possible to determine if the reference points are positioned in or out of the plane because of the inability to visualize depth.

Figure 10A:
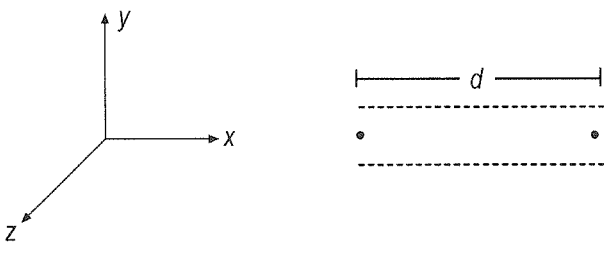
FIG. 10A-C is a schematic illustration of ambiguities that may occur in and out of an imaging plane.
Figure 10B:
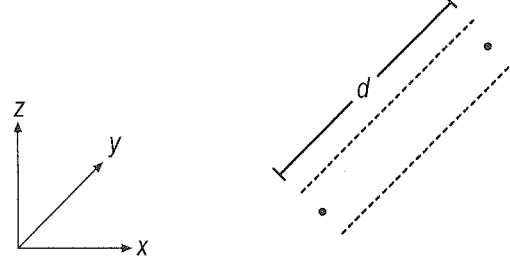
Figure 10C:
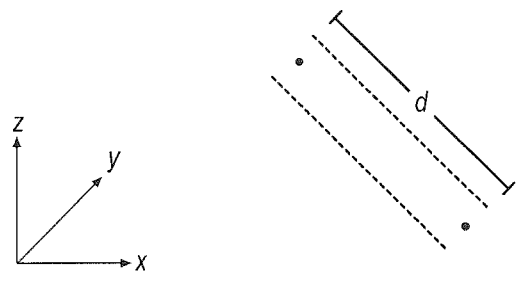

More specifically, referring to FIG. 10A, a projection to the x-y image plane is shown. However, the actual depth of the reference points along the z-axis is not possible to determine, even if the distance in the projected plane, d', and the actual distance between the features, d, is known. For example, because the reference point on the right side of the image could be lower or higher than the reference point on the left side of the image, as demonstrated in FIGS. 10B-10C.

There are many methods that may be utilized to track the flexible devices 100 in an image. Exemplary methods include placing specific markers or features, based on color, shape, location, or a combination of thereof, on the flexible device 100 and designing computer vision methods to track those markers and/or features. Other techniques require segmentation of the flexible device 100 from the background using shape, color, density, or motion information and then locating features within the flexible device 100 by exploiting the segmentation.

Another exemplary method is active contour tracking, which is augmented with template matching tuned to the flexible device. Many flexible devices 100 show up in fluoroscopy images as a single solid or textured compound curve. Thus, in such cases it may be useful to track the flexible device 100 shape with an active contour and then locate the specific features on the flexible device 100 with template matching techniques. An active contour is a method of maintaining a set of points on a curve by minimizing an energy function. Terms of the energy function maintain spacing between the points, minimize curvature (since flexible devices 100 resist sharp bends), and proximity to the curve in the image. The end result is a sequence of points that tracks the flexible device 100 and grows or shrinks as the projection of the flexible device 100 grows and shrinks. An active contour can be designed to track edges in the image (using an energy term that is minimized when on an edge) or, in the case of flexible devices 100, two edges with a darker area inside them. Active contour tracking is described in co-pending U.S. patent application Ser. No. 13/832,586, issued as U.S. Pat. No. 9,629,595 on Apr. 25, 2017, the contents of which are incorporated by reference in its entirety.

An active contour allows tracking of specific flexible device features 100, such as control rings, markers, or other distinctive features that show up in images, by reducing the search space for image template matching techniques, for example by defining a "local area". Techniques such as correlation coefficients may be used to match specific image features by generating a template image based on heading and construction of the flexible device 100 in the local area of the active contour and finding the position where it best matches the image. This technique results in robust tracking of the shape of the flexible device 100 with a reduced search space for tracking specific features.

Active contour guided template matching is effective in that the active contour provides a good estimate of heading in two dimensions while the template matching provides a good estimate of feature position within two dimensions. Thus the overall system is much more robust to disturbances and can recover lost features faster. Initialization of the tracker can use a human interface or image search for specific features to seed the tracker.

Linear Model of Heading with Angle and Tension

The three to four degrees of freedom information that are acquired from imaging (x and y position, orientation angle around the z axis, and a partial, or ambiguous, position and orientation in z axis), when augmented with elongation measurements, provide full localization. One way of processing elongation measurements from a flexible device 100 is to fit a linear model to the relationship between the displacement and force on the elongation measurements and the orientation of a sensor.

A simple linear model of a planar, two-pull wire flexible device is:

$$\theta = a_0 x_0 + a_1 \tau_0 + a_2 x_1 + a_3 \tau_1 + a_4 \tag{9}$$

where $a_i$ represents the constants to the linear equations, $x_k$ represents wire displacements, $T_k$ represents wire tensions, and $\theta$ represents estimated orientation of the flexible device 100. $a_i$ can be determined experimentally using a least-squares fit.

The model may be improved if it is known that pairs of pull-wires are antagonistic, or located on opposite sides of the flexible device 100. In that case, the coefficients of the antagonistic displacements or tensions should be equal and opposite. Equation 9 may be simplified using this information to:

$$\theta = a_0(x_0 - x_1) + a_1(\tau_0 - \tau_1) + a_2 \tag{10}$$

The primary assumption in Equation 10 is that bending will be entirely kinematic—there will be no torsion around the axis of the flexible device 100. In this way, it is possible to represent angle as a two-dimensional vector in the plane perpendicular to the flexible device 100 at the base of an articulating section. A pseudo-angle vector, $\vec{\theta}=[\theta_x,\ \theta_y]$ where the magnitude of $\vec{\theta}$ corresponds to the amount of rotation around the vector defined by $unit(\vec{\theta})$. In this representation, it is possible to represent of $\theta_x$ and $\theta_y$ into two equations:

$$\theta_x = a_0(x_0 - x_2) + a_1(x_1 - x_3) + a_2(\tau_0 - \tau_2) + a_3(\tau_1 - \tau_3) + a_4 \quad (11)$$

$$\theta_y = b_0(x_0 - x_2) + b_1(x_1 - x_3) + b_2(\tau_0 - \tau_2) + b_3(\tau_1 - \tau_3) + b_4 \quad (12)$$

Note that each of $\theta_x$ and $\theta_y$ is expressed as a function of all pull-wire measurements because of the inability to decouple angle directions from the pull wire directions.

The linear model works relatively well, provided that the underlying system is linear. Thus for systems incorporating metal pull-wires and limited friction, the linear model may be applicable. In systems with non-linear pull-wires or complicated friction characteristics (such as coil tubes) a non-linear model may be utilized. However, elongation elements cannot capture the roll angle from torsion. If there is limited torsion however, a linear model is effective for computing the orientation of the distal tip of a flexible device 100 in relation to the proximal end.

Filtering Image Information and Elongation Measurements

While image processing techniques can yield two dimensional position and orientation in a plane (plus some depth information) and a linear model of the flexible device 100 may estimate heading, the combination of the data yielded from the two techniques can produce a much stronger localization estimate. Indeed, the goal of localization estimation is to represent possible configurations of the flexible device 100 given the inputs of imaging data and elongation data and then correlate the two inputs to reduce the number of possibilities. While the elongation measurements map from a proximal device frame to a distal robot frame and the image processing maps from a global (image) frame GF to a distal robot frame, there is enough common information to provide a final mapping from the global frame to the distal device frame, thereby yielding an information filter using the image as one input and the elongation measurements as the second input.

Filtering techniques needed in this case require the ability to represent multi-modal hypotheses. An illustration for using multi-modal hypotheses is provided in FIG. 10. Because it is ambiguous whether the flexible device 100 is projected in or out of a given plane, two or more separated hypotheses are needed until more information is known. There are many ways of managing a filter with multiple hypotheses, including, but not limited to, the use of multiple Kalman filters, particle filters, and combinations of Gaussians.

Figure 11:
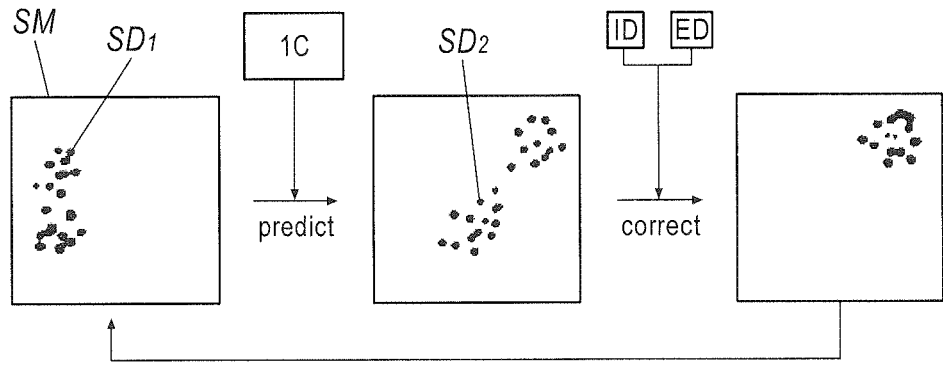
FIG. 11 is a schematic illustration of an particle filter for filter image and elongation measurements.

In one exemplary configuration, particle filters are used. Particle filters maintain a sampling of a hypothesis space using particles, or discrete estimates. This sampling of a hypothesis space is updated using probability-based coefficients based on expected changes in state and future measurements. The result is a sequence of prediction-correction steps that causes the distribution to converge to the most likely hypothesis or hypotheses. Thus particle filters are well suited to the problem of combining image localization information with elongation measurements. The basic steps of a particle filter technique is represented in FIG. 11.

More specifically, while a single set of static measurements SM (images and elongation displacements and tensions) can provide valuable information, additional information may be gleaned when the system moves. For example, referring to FIG. 11, initial measurements of a flexible catheter 100 may be represented by an initial sample distribution SD$_1$. An input command IC may be directed to move the flexible catheter 100. Based on the initial data from the sample distribution SD$_1$, an updated sample distribution SD$_2$ is generated to predict the movement of the catheter. Next, image data ID and elongation data ED collected may be combined together. The image data ID and elongation data ED may then be used to correct or update the sample distribution SD$_3$ to provide a more accurate representation of the flexible device 100. The updated sample distribution SD$_3$ may then be used as the initial data to repeat the process.

As a further example, if an initial roll orientation of the pull wires is known in relation to the flexible device 100 tip it is possible to recover all six degrees of freedom for localization, but if this roll is unknown or difficult to determine, only five degrees of freedom may be recovered. In contrast, if the system moves, the uncertainty about motion may be compensated in a particle filter by spreading particles in the different possible roll directions. The next set of measurements will then reduce the possibilities related to the roll degree of freedom. This is technique is similar to what is described above in connection with FIG. 8.

Bowden Coil Supported Tendons

Using fluoroscopy with any number of computer vision algorithms such as those described above, a planar position and heading of a flexible device 100 may be estimated. If the flexible device 100 is a catheter that has one or more articulating segments that are steered by tendons supported by Bowden Coils, information from these mechanical elements may also be used to improve a location estimation by convex optimization.

More specifically, in a vascular procedure there is a proximal portion of the vasculature where a catheter 100 may be inserted without articulation moving toward an anatomical location of interest. During this insertion, a robot can be used to position the tendons so that all tension is removed from the catheter to maintain maximum flexibility during this "passive" insertion. Once the anatomical location of interest has been reached, such as a calcified bifurcation for example, it may be necessary to begin controlled articulation of the catheter 100 to select a branch into which the catheter 100 may be directed. During controlled articulation, it can be helpful to know the location/orientation of the catheter 100 in the anatomy. This may be accomplished using the framework of FIG. 2 whereby the Remote Localization Measurement 110 is obtained from fluoroscopy processed with computer vision algorithms, and the "Elongation Measurement" 112 is obtained from tendon displacements and force.

Once passive insertion is completed, the (while at zero force) can be recorded as a starting tendon position for zero articulation. This will baseline for future tendon motions that articulate the catheter. The fluoroscopic image can, at that point, be processed to obtain a planar position and angle of the flexible device 100. The localization "signal processing" algorithm may be seeded by assuming that the articulating segment of the catheter 100 lies in the image plane and has zero roll. Therefore, at this first instant, a complete estimate for the orientation of the catheter tip, which would be in the plane of articulation with zero roll, may be determined. This technique assumes that the orientation of the distal termination of the Bowden Coils is coincident with catheter tip to begin.

The next step in the procedure is to apply controlled articulation to access the vessel of interest. At this point, force is applied to the tendons. The pitch, yaw, and roll of the distal tip relative to the reference frame of the distal termination of the Bowden Coils may be estimated based on the tendon displacements and forces using a method, such as, for example, a linear model discussed above. If the initial starting point for the Bowden and tendon termination frames were incorrect, then the fluoroscopy measurements will not coincide with the prediction from the elongation measurements, generating an error signal. This error signal can be used in a convex optimization routine that will generate a new estimate for the Bowden frame that minimizes the error between the fluoroscopy measurement and distal tip estimate from the elongation information. As the catheter 100 is exercised about its workspace, the estimate for Bowden frame should converge so that the out of plane information may be presented to the "localization customer" 116.

Localization with Electromagnetic Sensors and Elongation Measurements

Figure 12:
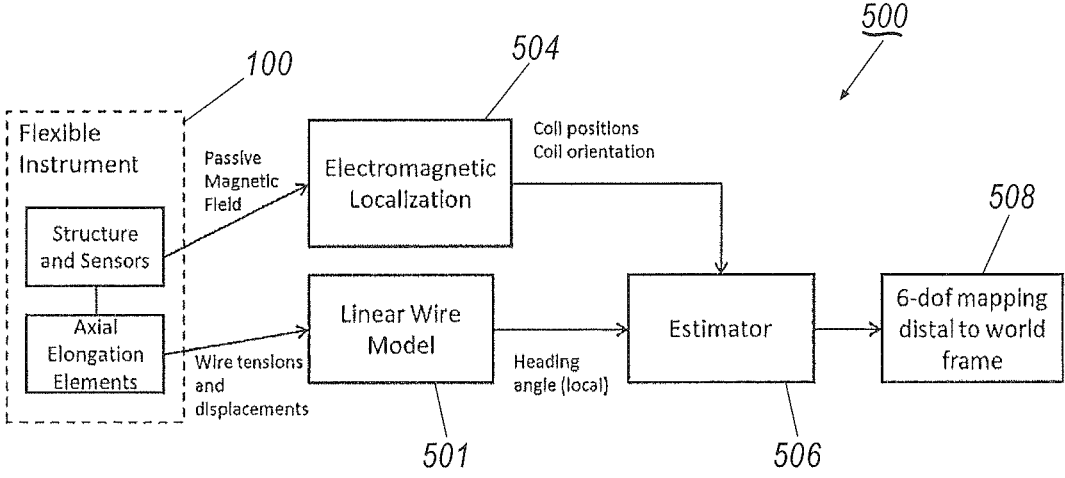
FIG. 12 is a schematic illustration of a system for localization of a flexible instrument using electromagnetic localization with linear wire model data.

With reference to FIG. 12, another proposed system 500 is illustrated that utilizes electromagnetic tracking as a remote localization measurement 504. The electromagnetic tracking is augmented with elongation measurements 501 by an estimator 506 to register a flexible device 100 to a target frame 508. In one exemplary configuration, 6 degrees of freedom of the flexible device 100 may be mapped to the global frame 508.

Electromagnetic (EM) trackers can produce up to six degrees of freedom of localization by embedding coils in the flexible device 100 and measuring induced currents from magnetic fields generated by transmitters. While it is possible for an EM tracker to provide all localization of a flexible device 100, in some situations it may be desirable to augment electromagnetic tracking with elongation measurements, as illustrated in FIG. 12.

Electromagnetic trackers are based on induced currents from a changing magnetic field. A current is induced in a receiver coil based on the change in magnetic flux through the coil. Typically, a transmitter turns on and off coils to produce magnetic fields with a known intensity and speed. Then, with knowledge of the size and orientation of the coil in relation to the flexible device 100, it is possible to estimate the location and/or orientation of the coil. For accuracy and more degrees of freedom, most EM systems use multiple transmitter coils and one or more receiver coils.

A single receiver coil coupled with a multi-coil transmitter can estimate five degrees of freedom-all localization except roll around the axis of the coil. Two or more receiver coils can estimate all six degrees of freedom if the coils are non-parallel, but often the accuracy of such systems is limited due to the size of the device 100. For instance, a typical flexible device requires very small coils if the device contains a center lumen—and the accuracy of the EM tracker is related to the amount of area enclosed within the coil. The result is that small coils are limited in range from the transmitter and other equipment or ferromagnetic materials in the area can cause warping of the magnetic field and the localization measurements.

Single-Coil Roll Estimation

In the case where only a single coil is incorporated in the device (or multiple coils that are non-collocated and parallel) the EM tracking system will not be able to localize roll. In these situations, the elongation measurements would be useful to determine the roll. It is important to note that the roll of the flexible device cannot be recovered without motion in the flexible device 100 because only the correlation of EM tracker motion and elongation measurement motion allows recovery of roll.

Figure 13:
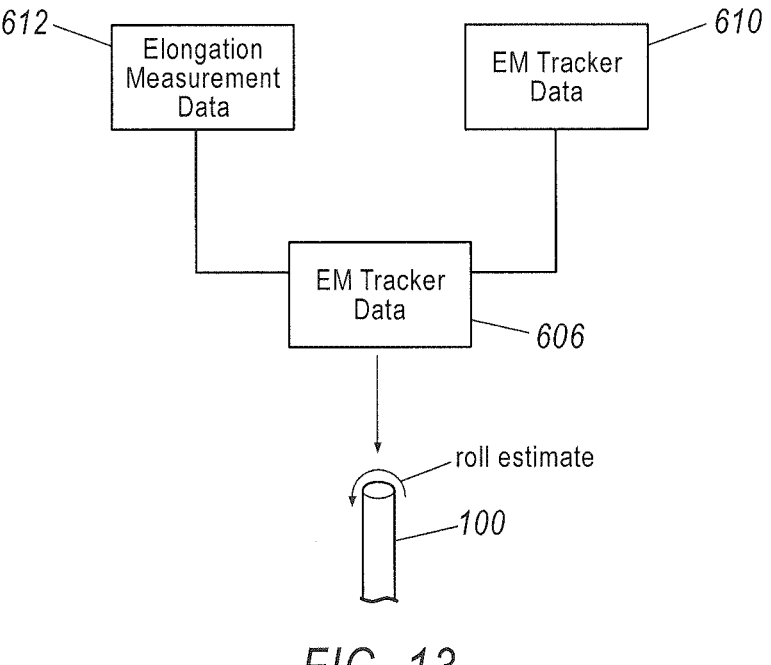
FIG. 13 is a schematic illustration of a system for using elongation measurement with electromagnetic localization data to determine roll estimation of a flexible instrument.

Since the two sensing modalities, namely electromagnetic localization 504 and linear wire modeling 502, must be correlated with respect to motion, algorithms are needed that can maintain hypotheses of the current roll and update that distribution of hypotheses with each new piece of sensory information. Many types of filters or estimators 506 could be used to maintain this distribution of hypotheses, such as, for example, Kalman filters and particle filters. It is also possible to record recent motions of the flexible device 100 and solve for the current roll angle using regression techniques such as non-linear least squares. Visually, this technique is shown in FIG. 13.

As an example, a flexible device 100 with a single coil at the tip would allow all localization except for the roll axis. Moving the device (either manually or robotically) would cause both the EM sensor and elongation measurements to change, reflecting a change in position in each of their coordinate systems. Specifically, the EM sensor would have a new position and heading in the global coordinate system 610, while the elongation measurements would reflect a new heading and orientation in the proximal device coordinate system 612. If the device coordinate system was known in relation to the global coordinate system, the motion could be correlated between the two sensing modalities. For a given motion, there would be a specific roll angle that would be consistent with the motion. By combining multiple measurements over time, an estimator 606/506 could keep the roll angle updated, even as the roll angle changes as the flexible device 100 moves.

Multi-coil Disturbance Rejection

The primary disturbances in EM tracker measurements are due to magnetic interference and electrical interference. Electrical interference causes noise in the measurements and often can be filtered out, but for faster motion, the elongation measurements could be used to provide higher frequency information than the EM tracker can provide on its own.

Another application for elongation measurements in conjunction with an EM tracker is in rejecting warping of the localization field due to changes in the magnetic field. Since EM trackers depend on magnetic fields in the area, and large bodies of ferromagnetic metal can warp this field, often the types of equipment in an operating room can disturb or change the localization as they move. For example, as a C-arm of a fluoroscopy system is rotated around a patient or moves closer or further from the patient, the magnetic field (and hence localization) is warped. By maintaining knowledge of elongation measurements, detection of the magnetic field being warped may be detected, even when the flexible device 100 is not moving. Thus localization field warping may be compensated for in software.

Localization with Maps and Elongation Measurements

As discussed above, elongation measurements can provide information about the deformation of a flexible medical device. If the device is operating in a region of the anatomy whose walls are sufficiently rigid so as to constrain the device, then a map of that anatomy can also provide information about the possible shapes the device may assume. The map may be obtained from pre-operative imaging, for example, from a CT scan; or intra-operatively, for example, from multiple views of contrast-enhanced 2D images or by collecting surface points using EM sensors. By correlating elongation measurements with shapes allowed by the anatomical map at different locations, an estimate of the shape of the device and its position within the map may be determined.

Figures 14A, 14B, 14C:
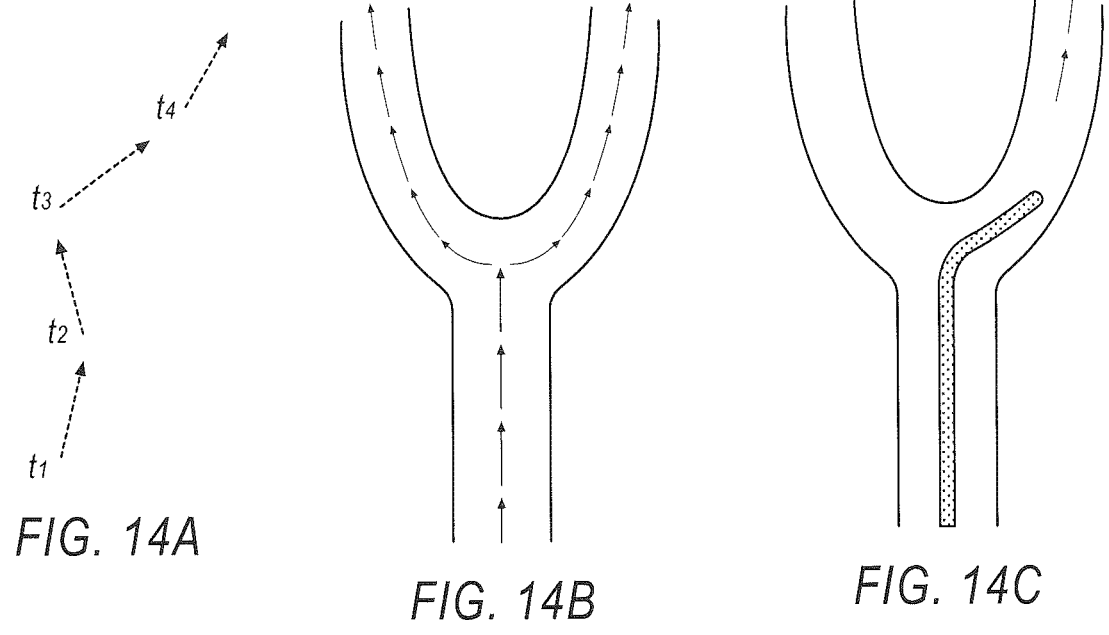
FIG. 14A illustrates elongation measurements of a flexible device taken over time.
FIG. 14B is an illustration of an anatomical map of a vessel.
FIG. 14C is an illustration of localization of a device within a map.

An example is use of elongation measurements are shown in FIG. 14. More specifically, FIG. 14A illustrates elongation measurements that continuously provide a 2 degree of freedom tip heading angle as a catheter 100 advances from time $t_i$ to $t_4$. FIG. 14B illustrates a map of the vessel in which the catheter is navigating. By finding the best match between the measured heading angles over time in FIG. 14A and the gradient of the center line of the map shown in FIG. 14B, the current tip position within the anatomy can be determined, as illustrated in FIG. 14C. Additionally, if the elongation measurements are noisy, imprecise, or reliable only within a plane, the shape estimate derived from the history of heading angles shown in FIG. 14A can be improved based on the corresponding gradients of the center line of the map shown in FIG. 14B.

It will be appreciated that the surgical instrument and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A method of tracking a flexible elongate instrument, the method comprising:

obtaining a first time history of remote localization measurement data of the flexible elongate instrument;

obtaining a second time history of elongation measurement data of the flexible elongate instrument; and combining the first time history of the remote localization measurement data with the second time history of the elongation measurement data to produce a localization of the flexible elongate instrument in a single coordinate frame.

2. The method of claim 1, further comprising outputting the localization of the flexible elongate instrument to a localization consumer.

3. The method of claim 1, further comprising determining roll of the flexible elongate instrument based on the elongation measurement data.

4. The method of claim 1, wherein the elongation measurement data is obtained from a measurement of displacement of a tendon or a force exerted on the tendon.

5. The method of claim 1, wherein the elongation measurement data includes at least one of displacement of a Bowden coil, tendon displacement, displacement data of an electrical lead, pressure measurement of a gas filled lumen, pushrod displacement data, or fiber optic displacement.

6. The method of claim 1, wherein the elongation measurement data is obtained from a fiber optic strain measurement device.

7. The method of claim 1, wherein the remote localization measurement data is obtained from at least one of an optical fiber, an electromagnetic sensor, a fluoroscopy system, or visual light cameras.

8. The method of claim 1, wherein the remote localization measurement data is registered to a remote localization frame, and wherein the elongation measurement data is registered to an elongation reference frame.

9. The method of claim 8, wherein combining the first time history of the remote localization measurement data with the second time history of the elongation measurement data further comprises registering the elongation reference frame to the remote localization frame.

10. The method of claim 1, wherein combining the first time history of the remote localization measurement data with the second time history of the elongation measurement data further comprises transforming the combined data to a global reference frame.

11. The method of claim 10, wherein the global reference frame includes at least one of a reference frame for an imaging technology or a reference frame for a patient.

12. The method of claim 1, wherein a signal processing system translates elongation measurements into an expected motion.

13. The method of claim 12, further comprising determining an orientation based on the expected motion.

14. The method of claim 1, wherein the localization of the flexible elongate instrument has more degrees of freedom than the remote localization measurement data.

15. The method of claim 14, wherein the remote localization measurement data comprise five degrees of freedom or fewer.

16. A method of tracking a flexible elongate instrument, the method comprising:

acquiring, via a remote system, time course localization data of the flexible elongate instrument;

obtaining time course elongation data of the flexible elongate instrument along a longitudinal axis of the flexible elongate instrument; and combining the time course localization data with the time course elongation data to produce a localization of the flexible elongate instrument in a single coordinate frame.

17. The method of claim 16, wherein the time course elongation data is indicative of at least one of a bending, deflection, or shape of the flexible elongate instrument.

18. A method of tracking a flexible elongate instrument, the method comprising:

obtaining a first time history of remote localization measurement data of the flexible elongate instrument;

obtaining a second time history of elongation measurement data of the flexible elongate instrument;

combining the first time history of the remote localization measurement data with the second time history of the elongation measurement data to produce a localization of the flexible elongate instrument in a single coordinate frame;

outputting the localization of the flexible elongate instrument to a localization consumer; and determining roll of the flexible elongate instrument based on the elongation measurement data.

19. The method of claim 18, wherein the localization consumer includes at least one of a robot control system, a sensing system, or a graphical display.

20. The method of claim 18, wherein the localization of the flexible elongate instrument has more degrees of freedom than the remote localization measurement data.

* * * * *